United States Patent
Chan et al.

(10) Patent No.: US 8,488,126 B2
(45) Date of Patent: Jul. 16, 2013

(54) OPTICAL IMAGE MEASUREMENT DEVICE INCLUDING AN INTERFERENCE LIGHT GENERATOR

(75) Inventors: Kinpui Chan, Ridgewood, NJ (US); Yasufumi Fukuma, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 285 days.

(21) Appl. No.: 12/733,051

(22) PCT Filed: Aug. 1, 2008

(86) PCT No.: PCT/JP2008/002086
§ 371 (c)(1),
(2), (4) Date: Feb. 4, 2010

(87) PCT Pub. No.: WO2009/019847
PCT Pub. Date: Feb. 12, 2009

(65) Prior Publication Data
US 2010/0134802 A1    Jun. 3, 2010

(30) Foreign Application Priority Data
Aug. 6, 2007    (JP) .................. 2007-204507

(51) Int. Cl.
*G01B 11/02*    (2006.01)
*G01B 9/02*    (2006.01)

(52) U.S. Cl.
USPC ........................................ 356/497; 356/479

(58) Field of Classification Search
USPC .. 356/479, 497; 250/227.19, 227.27; 600/476
See application file for complete search history.

(56) References Cited

U.S. PATENT DOCUMENTS

| 5,381,229 | A  | * | 1/1995  | Murphy et al. ............... 356/477 |
| 5,633,712 | A  | * | 5/1997  | Venkatesh et al. ............ 356/503 |
| 5,748,598 | A  |   | 5/1998  | Swanson et al. |
| 6,134,003 | A  |   | 10/2000 | Tearney et al. |
| 6,490,046 | B1 | * | 12/2002 | Drabarek et al. ............. 356/489 |
| 7,426,036 | B2 | * | 9/2008  | Feldchtein et al. ........... 356/479 |

(Continued)

FOREIGN PATENT DOCUMENTS

| EP | 1677095 A1  | 7/2006  |
| EP | 1 852 692 A1 | 11/2007 |

(Continued)

OTHER PUBLICATIONS

Tanno, N., "Kogaku," Japanese Journal of Optics, vol. 28, Issue 3, p. 116 (1999).

(Continued)

*Primary Examiner* — Michael A Lyons
(74) *Attorney, Agent, or Firm* — Edwards Wildman Palmer LLP

(57) ABSTRACT

An optical image measurement device 1 causes an interference light generator to split a low-coherence light into a signal light and a reference light, and superimposes the signal light propagated through a measured object 5000 and the reference light propagated through the reference mirror 9 to generate an interference light. Two-dimensional photosensor arrays 14 and 15 detect the interference light. A computer 16 forms an image of the measured object 5000 based on the detection result. By inserting the optical fiber bundle 5 into the measured object 5000 to perform a measurement, a tomographic image of a deep tissue of the measured object 5000 can be obtained. Furthermore, the optical image measurement device 1 can form a high-resolution image of the deep tissue of the measured object 5000 because performing a measurement using the OCT technology.

7 Claims, 10 Drawing Sheets

U.S. PATENT DOCUMENTS

| | | | |
|---|---|---|---|
| 7,508,523 B2 * | 3/2009 | Chang et al. | 356/479 |
| 2003/0011782 A1 | 1/2003 | Tanno | |
| 2003/0137669 A1 * | 7/2003 | Rollins et al. | 356/479 |
| 2007/0008545 A1 | 1/2007 | Feldchtein et al. | |
| 2007/0070295 A1 | 3/2007 | Tsukada et al. | |
| 2007/0159597 A1 | 7/2007 | Fukuma et al. | |
| 2008/0024788 A1 | 1/2008 | Shimizu et al. | |
| 2008/0031410 A1 | 2/2008 | Shimizu et al. | |
| 2008/0252901 A1 | 10/2008 | Shimizu et al. | |
| 2009/0273790 A1 | 11/2009 | Shimizu et al. | |

FOREIGN PATENT DOCUMENTS

| | | |
|---|---|---|
| JP | 06-035946 | 5/1994 |
| JP | 09-119813 | 5/1997 |
| JP | 2000-503237 | 3/2000 |
| JP | 2000-131221 | 5/2000 |
| JP | 2001-046321 | 2/2001 |
| JP | 2001066245 A | 3/2001 |
| JP | 2001-125009 | 5/2001 |
| JP | 2001-228080 | 8/2001 |
| JP | 2001-330558 | 11/2001 |
| JP | 2003172690 A | 6/2003 |
| JP | 2004-317437 | 11/2004 |
| JP | 2004-344260 | 12/2004 |
| JP | 2005156540 A | 6/2005 |
| JP | 2006-047264 A | 2/2006 |
| JP | 2006-184284 A | 7/2006 |
| JP | 2006-191937 A | 7/2006 |
| JP | 2007-117714 A | 5/2007 |
| JP | 2007-125277 | 5/2007 |
| JP | 2007-185244 A | 7/2007 |
| WO | WO-2005031320 A1 | 4/2005 |
| WO | WO-2006/024014 A2 | 3/2006 |
| WO | WO-2006/077921 A1 | 7/2006 |

OTHER PUBLICATIONS

Chan et al., K.P., "Micrometre-resolution, optical imaging of objects through highly scattering media using a heterodyne detector array," Electronics Letters, vol. 30, p. 1753, (1994).

International Search Report dated Nov. 4, 2008, issued in International Patent Application No. PCT/JP2008/002086.

Office Action (Notification of Reasons for Rejection) issued for Japanese Patent Application No. 2007-204507.

Supplementary European Search Report dated Apr. 9, 2013, issued for the corresponding European patent application No. 08 79 0350.6.

Office Action mailed Jun. 4, 2013, issued for the corresponding Japanese patent application No. 2007-204507.

* cited by examiner

RELATED ART

OPTICAL IMAGE MEASUREMENT DEVICE INCLUDING AN INTERFERENCE LIGHT GENERATOR

TECHNICAL FIELD

The present invention relates to an optical image measurement device that forms an image of a measured object by using the OCT (Optical Coherence Tomography) technology.

BACKGROUND ART

In recent years, an optical image measurement technology of forming an image of the surface or inside of a measured object by using a laser light source or the like has gained attention. The optical image measurement technology is expected to be applied particularly in the medical field because this technology is noninvasive to a human body unlike the conventional X-ray CT technology.

An example of typical methods relating to the optical image measurement technology is the OCT technology (referred to as the "optical coherence tomographic imaging method" or the like). This technology makes it possible to detect a reflected light or a transmitted light by a measured object with excellent distance resolution in the μm order by utilizing the low coherency of a broadband light source having a broad spectrum width, such as a Super Luminescent Diode (SLD) (refer to Non-Patent Document 1, for example).

As an example of a device utilizing the OCT technology, a conventional optical image measurement device using a Michelson-type interferometer will be described. The basic configuration of the optical image measurement device is shown in FIG. 10. An optical image measurement device 1000 shown in FIG. 10 is a device that forms an image of a measured object 1005, and includes a broadband light source 1001, a mirror 1002, a beam splitter 1003, and a photodetector 1004. A light beam emitted from the broadband light source 1001 is split into a reference light R and a signal light L by the beam splitter 1003. The reference light R travels toward the mirror 1002. The signal light S travels toward the measured object 1005.

As shown in FIG. 10, a traveling direction of the signal light S is defined as the z-direction and a plane orthogonal thereto is defined as the x-y plane. The mirror 1002 can be displaced by a not-shown drive mechanism in the directions of an arrow pointing to both sides in FIG. 10. This is referred to as a z-scan.

The reference light R is subjected to the Doppler frequency shift by the z-scan when reflected by the mirror 1002. On the other hand, the signal light S is reflected by the surface and inner layer of the measured object 1005. The measured object 1005 is a scattering medium, and the reflected light of the signal light S is assumed to have a diffusion wave front with a rough phase including multiple scattering. The signal light S propagated through the measured object 1005 and the reference light R propagated through the mirror 1002 are superimposed by the beam splitter 1003 to become an interference light.

In an image measurement using the OCT technology, only such components of the signal light S that a difference in optical path length between the signal light S and the reference light R is within the μm-order coherent length (coherence length) of the light source and that have a phase correlation with the reference light R, cause interference with the reference light R. That is to say, only coherent signal light components of the signal light S selectively interfere with the reference light R. According to this principle, by executing a z-scan at the position of the mirror 1002 and changing the optical path length of the reference light R, the light reflection profile of the inner layer of the measured object 1005 is measured. Furthermore, it is also possible to scan with the signal light S in the x-y plane direction. By detecting the interference light while executing such scans in the z-direction and in the x-y plane direction and analyzing the detection result (heterodyne signals), it is possible to form a two-dimensional tomographic image of the measured object 1005 (refer to Non-Patent Document 1).

According to the above method, sequential measurements of various sites in the depth direction (z-direction) and tomographic plane direction (x-y plane direction) of the measured object 1005 is required, and therefore, there is a problem with a longer measurement time. In view of the measurement principle, it is difficult to shorten the measurement time.

A method for solving this problem has been also devised. The basic configuration of a device employing this method is shown in FIG. 11. This optical image measurement device 2000 includes a xenon lamp 2001, a mirror 2002, a beam splitter 2003, a two-dimensional photosensor array 2004, and lenses 2006 and 2007. On the light-receiving surface of the two-dimensional photosensor array 2004, a plurality of light-receiving elements are arranged.

A light beam emitted from the light source 2001 is converted into a parallel light flux with a beam diameter expanded by the lenses 2006 and 2007. The beam splitter 2003 splits this parallel light flux into the reference light R and the signal light S. The signal light S is radiated to a range corresponding to the beam diameter. Therefore, the signal light S propagated through the measured object 2005 includes information on the measured object 2005 in the radiated range.

The reference light R and the signal light S are superimposed by the beam splitter 2003 to become an interference light. This interference light has a beam diameter corresponding to the signal light S or the like. The two-dimensional photosensor array 2004 detects the interference light by the two-dimensional light-receiving surface. Based on the detection result, a tomographic image of the measured object 2005 in the abovementioned radiated range is formed. Therefore, it is possible to speedily acquire a tomographic image of the measured object 2005 without scanning with the light beam.

As an example of such a non-scanning optical image measurement device, a device described in Non-Patent Document 2 is known. This device is configured to input a plurality of heterodyne signals outputted from a two-dimensional photosensor array into a plurality of signal processing systems arranged in parallel and detect the amplitude and phase of each of the heterodyne signals.

However, in order to enhance the spatial resolution of an image in such a configuration, it is necessary to increase the number of elements of the array, and furthermore, it is also necessary to install a signal processing system provided with such a number of channels that corresponds to the number of the elements. Therefore, it is difficult to achieve satisfactory resolution in the medical field, industrial field and so on.

Accordingly, the inventors proposed the non-scanning optical image measurement device as described below in Patent Document 1. This optical image measurement device comprises: a light source that emits a light beam; an interference optical system that splits the light beam emitted from the light source into a signal light travelling through a subject placement position where a subject is placed and a reference light travelling along an optical path different from an optical path through the subject placement position, and superimposes the signal light propagated through the subject placement position and the reference light propagated on the different optical path to generate an interference light; a frequency shifter that the interference optical system relatively shifts the frequency of the signal light and the frequency of the reference light; an opto-isolator that splits the interference light into two and periodically interrupts the split interference light to generate two lines of interference light pulses with a phase difference of 90 degrees between the lines so that the interference optical system receive the interference light; photosensors that receive the two lines of interference light pulses, respectively; and a signal processor that the photosensors are spatially arranged, each having a plurality of light-receiving elements that independently obtain light-receiving signals, and a plurality of light-receiving signals obtained by the photosensors are integrated to generate a signal corresponding to each point of interest on a propagation path of the signal light on the surface or in the inner layer of the subject placed on the subject placement position.

This optical image measurement device has a configuration that, in a configuration to split the interference light of the reference light and the signal light into two and receive by the two photosensors (two-dimensional photosensor arrays), the opto-isolator is placed in front of each of the sensor arrays to sample the interference light. Then, the device sets a phase difference of 702 in sampling cycle of the split two interference lights to detect the intensities of the signal light and the reference light composing the background light components of the interference light and the orthogonal components (sin component and cos component) of the phase of the interference light, and subtracts the intensities of the background light components included in the outputs from both the sensor arrays from the outputs of both the sensor arrays to calculate two phase orthogonal components of the interference light, thereby obtaining the amplitude of the interference light by using the calculation result.

As a two-dimensional photosensor array, a commercially available image sensor such as a CCD (Charge-Coupled Device) camera is widely used. However, currently available CCD image sensors have a low frequency response characteristic, and there has been a traditionally recognized problem in which the CCD image sensors are unable to follow a beat frequency of heterodyne signals of about a few KHz to a few MHz. It can be said that the optical image measurement device according to Patent Document 1 devised by the inventors is characterized in that the low response characteristic is utilized to conduct measurements upon full recognition of this problem.

The optical image measurement device as described above has an advantage of being capable of depicting the microstructure of a measured object, for example, acquiring an image at the cell level of a living body, but cannot image the structure of a deep part that a light radiated to the surface of the measured object cannot reach. For example, a conventional optical image measurement device can acquire an image of the fundus oculi, skin tissues and so on of a living body, but cannot image the deep tissue of an internal organ and so on.

In this specification, a site at a depth that a light radiated on the surface of a measured object cannot reach, namely, a site at a depth where an image cannot be acquired when a light is radiated from the surface may be simply referred to as a "deep part." The depth of the deep part varies depending on a measured object, and also varies depending on the wavelength and intensity of a light.

As a device for imaging the tissues of a deep part of a measured object, an endoscope is known. An endoscope is used to examine the inside of a body by inserting part of the device into an opening (a natural opening or an artificial opening) of the surface of a measured object (for example, refer to Patent Document 2).

An endoscope can thus image the structures of a deep part of a measured object, but cannot depict the microstructure, unlike an optical image measurement device.

[Patent Document 1] Japanese Unexamined Patent Application Publication 2001-330558
[Patent Document 2] Japanese Unexamined Patent Application Publication 2007-125277
[Non-patent Document 1] N. Tanno, "Kogaku", Vol. 28 Issue 3, 116 (1999)
[Non-patent Document 2] K. P. Chan, M. Yamada, H. Inaba, "Electronics Letters", Vol. 30, 1753 (1994)

DISCLOSURE OF THE INVENTION

Problem that the Invention is to Solve

The present invention has been developed to solve the problem as described above, and an object of the present invention is to provide an optical image measurement device capable of imaging the microstructure of a deep tissue of a measured object.

Means for Solving the Problem

In order to achieve the above object, in a first aspect of the present invention, an optical image measurement device comprises: an interference light generator configured to split a low-coherence light into a signal light and a reference light, and superimpose the signal light propagated through a measured object and the reference light propagated through a reference object to generate an interference light; a detector configured to detect the interference light; and an image forming part configured to form an image of the measured object based on a detection result of the interference light, wherein the interference light generator includes a light guiding part configured to emit the signal light split from the low-coherence light from one end and guide the signal light propagated through the measured object and entered into the one end, and the interference light generator is configured to superimpose the guided signal light and the reference light to generate an interference light.

Further, in a second aspect of the present invention, the optical image measurement device according to the first aspect is characterized in that the light guiding part has flexibility.

Further, in a third aspect of the present invention, the optical image measurement device according to the first aspect is characterized in that: the light guiding part includes a splitter configured to split a low-coherence light having entered from the other end into a signal light and a reference light, and the light guiding part is configured to guide the signal light propagated through the measured object and entered into the one end to the other end and emit the signal light therefrom and is configured to emit the reference light from the other end; and the interference light generator is configured to superimpose the signal light and the reference light emitted from the other end, respectively, to generate an interference light.

Further, in a fourth aspect of the present invention, the optical image measurement device according to the first aspect is characterized in that the light guiding part includes an optical fiber bundle.

Further, in a fifth aspect of the present invention, the optical image measurement device according to the third aspect is characterized in that: the light guiding part includes an optical fiber bundle having the one end and the other end as both ends thereof; and the splitter includes a reflecting part configured to reflect part of the low-coherence light guided to the one end and split the low-coherence light into a signal light and a reference light.

Further, in a sixth aspect of the present invention, the optical image measurement device according to the fourth aspect is characterized in that a microlens is disposed to the one end of each fiber of the optical fiber bundle.

Further, in a seventh aspect of the present invention, the optical image measurement device according to the fifth aspect is characterized in that a microlens is disposed to the one end of each fiber of the optical fiber bundle.

Further, in an eighth aspect of the present invention, the optical image measurement device according to the fourth aspect is characterized in that the detector includes a two-dimensional photosensor array configured to simultaneously detect a plurality of interference lights based on a plurality of signal lights guided by a plurality of fibers included in the optical fiber bundle.

Further, in a ninth aspect of the present invention, the optical image measurement device according to the fifth aspect is characterized in that the detector includes a two-dimensional photosensor array configured to simultaneously detect a plurality of interference lights based on a plurality of signal lights guided by a plurality of fibers included in the optical fiber bundle.

Further, in a tenth aspect of the present invention, the optical image measurement device according to the fourth aspect is characterized in that: the interference light generator is configured to cause a plurality of fibers included in the optical fiber bundle to sequentially guide signal lights; the detector is configured to sequentially detect interference lights based on the sequentially guided signal lights; and the image forming part is configured to sequentially form images of different sites of the measured object based on the respective interference lights detected sequentially.

Further, in an eleventh aspect of the present invention, the optical image measurement device according to the fifth aspect is characterized in that: the interference light generator is configured to cause a plurality of fibers included in the optical fiber bundle to sequentially guide signal lights; the detector is configured to sequentially detect interference lights based on the sequentially guided signal lights; and the image forming part is configured to sequentially form images of different sites of the measured object based on the respective interference lights detected sequentially.

Further, in a twelfth aspect of the present invention, the optical image measurement device according to the first aspect is characterized in that the interference light generator includes an optical member for matching an optical path length of the signal light with an optical path length of the reference light.

Further, in a thirteenth aspect of the present invention, the optical image measurement device according to the first aspect is characterized in that the interference light generator includes an optical member for matching an influence of dispersion applied to the signal light with an influence of dispersion applied to the reference light.

Further, in a fourteenth aspect of the present invention, the optical image measurement device according to the twelfth aspect is characterized in that the optical member is disposed on an optical path of the reference light.

Further, in a fifteenth aspect of the present invention, the optical image measurement device according to the thirteenth aspect is characterized in that the optical member is disposed on an optical path of the reference light.

Effect of the Invention

An optical image measurement device according to the present invention splits a low-coherence light into a signal light and a reference light, superimposes the signal light propagated through a measured object and the reference light propagated through a reference object to generate an interference light, detects this interference light, and forms an image of the measured object based on the result of the detection of the interference light. The image formed by the optical image measurement device is a high-resolution image by the OCT technology.

Furthermore, this optical image measurement device is provided with a light guiding part. This light guiding part is configured to emit a signal light split from the low-coherence light from one end and guide the signal light propagated through a measured object and entered from the one end. Then, this optical image measurement device acts to generate an interference light by superimposing the signal light guided by the light guiding part and the reference light. By employing such a configuration, it is possible to perform a measurement in a state that the light guiding part is placed near the deep tissue of the measured object.

According to the optical image measurement device described above, it is possible to image the microstructure of the deep tissue of the measured object.

DESCRIPTION OF REFERENCE NUMERALS AND SYMBOLS

Figure 1:
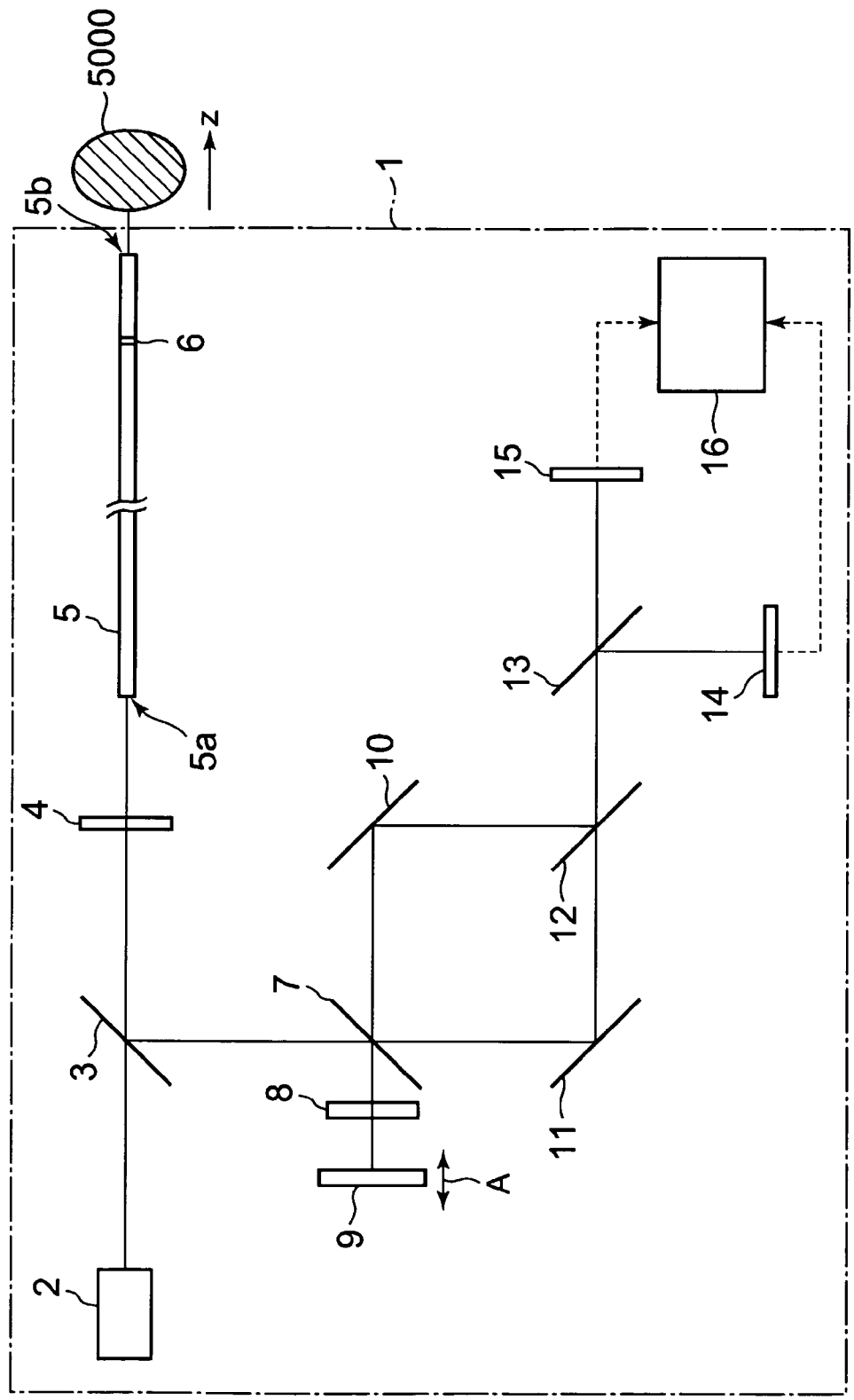
FIG. 1 is a schematic view illustrating an example of the configuration of a first embodiment of the optical image measurement device according to the present invention.

1: optical image measurement device
2: light source
3, 7, 12: beam splitters
4: polarization element
5: optical fiber bundle
5$a$: base end part
5$b$: top end part
5$\alpha$: optical fiber
5$\beta$: microlens
6: reflector
8: waveplate
9: reference mirror
10, 11: reflection mirrors
13: polarizing-beam splitter
14, 15: two-dimensional photosensor arrays
16: computer
17: controller
18: display
19: manipulation part
20: signal processor

BEST MODE FOR CARRYING OUT THE INVENTION

An example of an embodiment of the optical image measurement device according to the present invention will be described in detail with reference to the drawings.

The optical image measurement device according to the present invention is capable of acquiring an image of a deep part of a measured object like an endoscope, and also capable of imaging the microstructure thereof. Therefore, when applied in the medical field and the biological field, it is also capable of acquiring an image that represents the microstructure of an inner tissue of a living body (for example, an image at the cell level of an internal organ, the brain, or the like).

As an optical image measurement device utilizing the OCT technology, there are various types such as a Fourier-domain (frequency domain) type, a full-field type and a swept-source type, which are different in measurement mode.

A Fourier-domain optical image measurement device executes spectral resolution on an interference light and form an image based on the frequency distribution. The Fourier-domain device scans a measurement region of a measured object with a signal light to form an image, and forms an image of the measurement region. This type of optical image measurement device is disclosed in, for example, Japanese Unexamined Patent Application Publication No. 2007-117714.

A swept-source optical image measurement device also scans with a signal light to execute a measurement. The swept-source type, instead of executing spectral resolution on an interference light, uses a light source that switches and outputs lights of various frequencies at high speed (a high-speed wavelength scanning laser). This type of optical image measurement device is disclosed in, for example, Japanese Unexamined Patent Application Publication No. 2007-24677.

Further, the full-field optical image measurement device, as described in the aforementioned Patent Document 1, is featured by radiating a light flux having a certain beam diameter to a measured object and thereby being capable of forming an image of the radiated region at a time. With the Fourier-domain type and the swept-source type, an image of a cross-section extending in the depth direction of a measured object is obtained. On the other hand, with the full-field type, an image of a cross-section orthogonal to the depth direction is obtained. Also, with the full-field type, it is possible to scan with a signal light in order to change a measurement site of a measured object.

As a first embodiment according to the present invention, the full-field optical image measurement device will be described below. Further, as a second embodiment, the Fourier-domain and swept-source optical image measurement devices will be described.

First Embodiment

An application example of the present invention to the full-field optical image measurement device will be described.

[Device Configuration]

An example of the schematic configuration of the optical image measurement device according to this embodiment is shown in FIG. 1. This optical image measurement device 1 is a device for acquiring a tomographic image of a measured object 5000.

The optical image measurement device 1 is provided with a light source 2 that outputs a broadband light (a low-coherence light). The broadband light outputted from the light source 2 has a predetermined beam diameter.

The light source 2 includes, for example, a halogen lamp. This halogen lamp outputs a non-polarized broadband light. The light source 2 may include an optical fiber bundle that guides a light outputted from the halogen lamp, a Kohler illumination optical system for uniformly illuminating the radiation field of the outputted light, and so on.

Other than the halogen lamp, any light source that outputs a non-polarized broadband light may be used. For example, any thermal light source (a light source by black-body radiation) such as a xenon lamp may be applied. Moreover, it is also possible to use a light source that outputs a randomly polarized broadband light.

Here, the term "non-polarized" refers to a polarization state including a linearly polarized light, a circularly polarized light, and an elliptically polarized light. Moreover, the term "randomly polarized" refers to a polarization state having two linear polarization components orthogonal to each other, in which the power of each of the linear polarization components varies temporally at random (for example, refer to Japanese Unexamined Patent Application Publication No. 7-92656). Although only use of a non-polarized light will be described in detail below, similar action and effect can be obtained with a similar configuration in the case of a randomly-polarized light.

The broadband light outputted from the halogen lamp or the like includes various bands of lights. The light source 2 includes a filter that transmits only a predetermined band of this broadband light. The band transmitted by this filter is determined depending on the resolution, the measurement depth or the like and is set to, for example, a band whose central wavelength is about 760 nm and wavelength width is about 100 nm. In this case, in the depth direction of the measured object 5000 (the z-direction shown in FIG. 1) and in a direction orthogonal thereto (the lateral direction), images having resolution of about 2 μm can be acquired. The light transmitted through this filter is also referred to as the broadband light.

The broadband light outputted from the light source 2 is transmitted through a beam splitter 3 and a polarization element 4, and enters a base end part 5$a$ of an optical fiber bundle 5. For example, the polarization element 4 transmits only 45-degree linear polarization component of the broadband light.

The optical fiber bundle 5 is a bundle of a plurality of optical fibers. One end of each optical fiber is disposed to the base end part 5a, while the other end is disposed to a top end part 5b. The plurality of optical fibers are bundled so that the cross-sections thereof are arranged in an array.

As the optical fiber bundle 5, for example, one that is generally used in a device such as an endoscope can be applied (for example, refer to Japanese Unexamined Patent Application Publication No. 2006-130183). For example, the optical fiber bundle 5 is formed like a probe that can be inserted into a subject body, as in an endoscope, for example. The optical fiber bundle 5 (the probe) has flexibility like the probe of an endoscope, and can be formed so that the shape thereof can be deformed when inserted into a subject body. Moreover, it is also possible to install a mechanism for arbitrarily deforming the shape of the optical fiber bundle 5 (the probe). These configurations are similar to that of the probe of a conventional endoscope, for example.

The number of the optical fibers included in the optical fiber bundle 5 is one of the factors that determine the lateral resolution by the optical image measurement device 1. The optical fiber bundle 5 has an appropriate number of optical fibers in accordance with, for example, the use of the optical image measurement device 1. The optical fiber bundle 5 is an example of the "light guiding part" of the present invention.

The optical fiber bundle 5 is provided with a reflector 6. The reflector 6 reflects part of the broadband light traveling toward the top end part 5b in the optical fiber bundle 5. The broadband light reflected by the reflector 6 is used as a reference light. On the other hand, the broadband light transmitted through the reflector 6 is used as a signal light. The reflector 6 is an example of the "splitter" and "reflecting part" of the present invention.

The reflector 6 can be installed at any position of the optical fiber bundle 5. For example, as shown in FIG. 1, the reflector 6 may be installed at a position other than the end parts 5a and 5b of the optical fiber bundle 5, or may be installed at the top end part 5b or the like.

For example, the reflector 6 is formed by depositing a translucent film to the optical fiber bundle 5. It is also possible to use a half mirror as the reflector 6. For example, it is possible to apply a configuration in which the optical fiber bundle 5 is divided into a portion on the end part 5a side and a portion on the top end part 5b side and a half mirror is installed at the dividing position. Moreover, the half mirror may be installed, for example, between the top end part 5b and the measured object 5000, or between the base end part 5a and the polarization element 4.

The reference light composed of the broadband light reflected by the reflector 6 is emitted from the base end part 5a of the optical fiber bundle 5, transmitted through the polarization element 4, and reflected by the beam splitter 3. Furthermore, the reference light is reflected by a beam splitter 7 and transmitted through a waveplate (λ/4 plate) 8 to reach a reference mirror 9.

The reference light reflected by the reference mirror 9 is again transmitted through the waveplate 8, transmitted through the beam splitter 7 and reflected by a reflection mirror 10 to reach a beam splitter 12.

Figure 3:
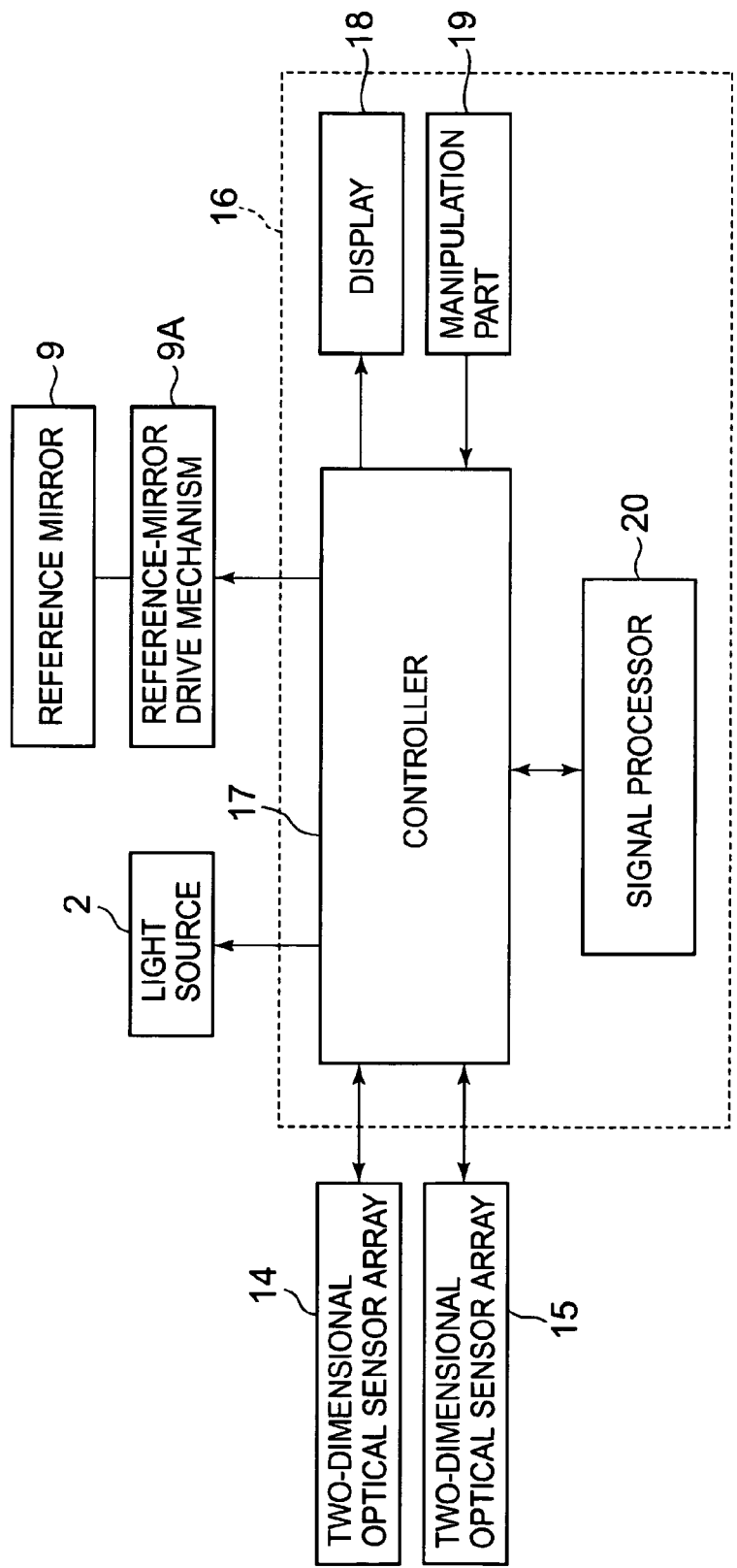
FIG. 3 is a schematic block diagram illustrating an example of the configuration of the first embodiment of the optical image measurement device according to the present invention.

The reference mirror 9 is configured to be movable in the direction of an arrow A pointing to both sides in FIG. 1 (refer to a reference mirror moving mechanism 9A shown in FIG. 3). Consequently, it is possible to acquire images at various depth positions of the measured object 5000. Further, it is possible to generate interference lights with different phases by changing the position of the reference mirror 9 (described later). The reference mirror 9 is an example of the "reference object" of the present invention.

The reference light having reached the beam splitter 12 is such a light that is initially a non-polarized broadband light, propagated through the polarizing plate 4, propagated through the polarizing plate 4 again and then propagated through the waveplate 8 twice. Accordingly, the reference light having reached the beam splitter 12 has a polarization property of circular polarization.

On the other hand, the signal light composed of the broadband light transmitted through the reflector 6 is emitted from the top end part 5b of the optical fiber bundle 5.

Figure 2:
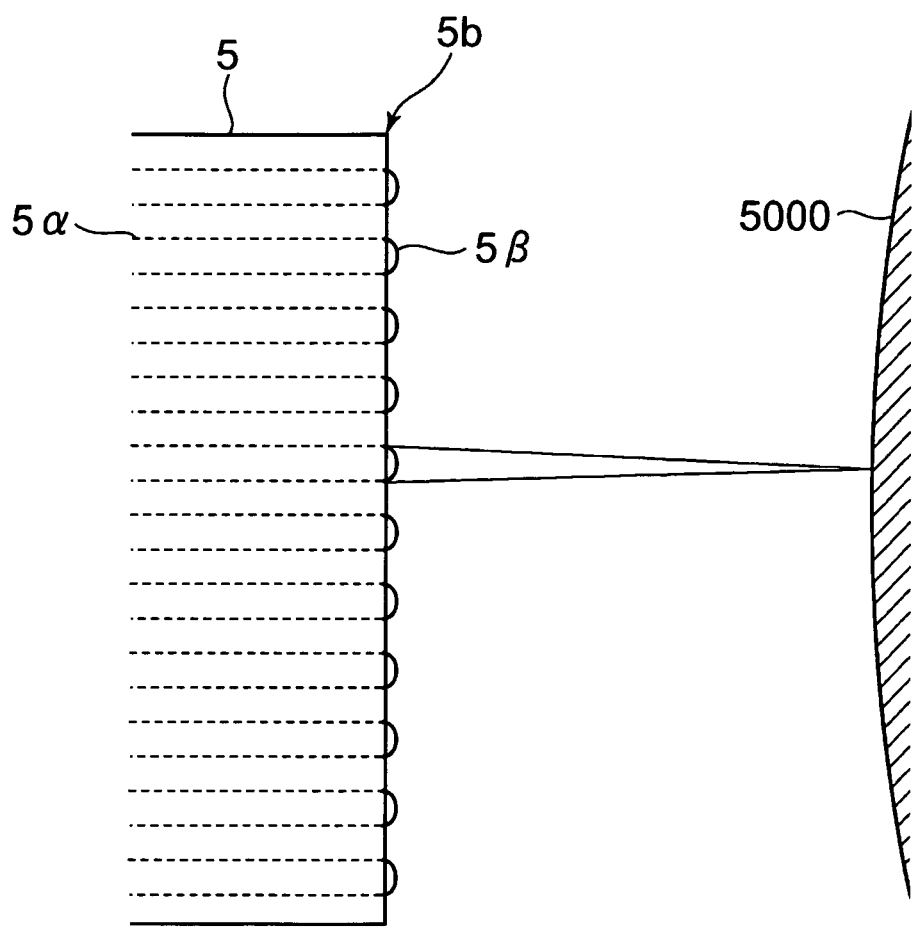
FIG. 2 is a schematic view illustrating an example of the configuration of the first embodiment of the optical image measurement device according to the present invention.

As shown in FIG. 2, to the top end part 5b of the optical fiber bundle 5, a microlens 5β is disposed to each optical fiber 5α of the optical fiber bundle 5. The microlens 5β acts as an objective lens to converge the signal light emitted from the top end part 5b side of the optical fiber 5α.

The signal light radiated to the measured object 5000 is reflected and scattered at various depth positions of the measured object 5000. The reflected light and scattered light of the signal light are propagated through the microlenses 5β, and enter the optical fibers 5α. Furthermore, the signal light is guided by the optical fiber bundle 5 and emitted from the base end part 5a.

The signal light emitted from the base end part 5a is transmitted through the polarization element 4, is reflected by the beam splitter 3, is transmitted through the beam splitter 7, is reflected by a reflection mirror 11, and reaches the beam splitter 12.

The signal light having reached the beam splitter 12 is such a light that is initially a non-polarized broadband light, propagated through the polarizing plate 4 (45-degree linear polarization), propagated through the measured object 5000, and then propagated through the polarizing plate 4 again. Accordingly, the signal light having reached the beam splitter 12 has a polarization property of linear polarization.

The reference light reflected by the beam splitter 12 and the signal light transmitted by the beam splitter 12 are superimposed with each other to become an interference light. This interference light is split into two polarization components by a polarizing-beam splitter 13 and detected by the two-dimensional photosensor arrays 14 and 15.

That is to say, an S-polarization component of the interference light are reflected by the polarizing-beam splitter 13 and detected by the two-dimensional photosensor array 14. On the other hand, a P-polarization component of the interference light are transmitted through the polarizing-beam splitter 13 and detected by the two-dimensional photosensor array 15.

Each of the two-dimensional photosensor arrays 14 and 15 has a two-dimensional light-receiving surface. The S-polarization component and the P-polarization component respectively include a corresponding number of beams to the number of the optical fibers 5α that have guided the signal light and the reference light. These beams are arranged similarly to the arrangement of the cross-sections of the optical fibers 5α.

When detecting the polarization components of the interference light, each of the two-dimensional photosensor arrays 14 and 15 sends signals (detection signals) representing the detection result to the computer 16.

Each of the two-dimensional photosensor arrays 14 and 15 is composed of any image pick-up element having a two-dimensional light-receiving surface. For example, it is possible to use a CCD image sensor, a CMOS (Complementary Metal Oxide Semiconductor) image sensor, or the like as the two-dimensional photosensor arrays 14 and 15.

The two-dimensional photosensor arrays 14 and 15 are examples of the "detector" of the present invention. The detector is not necessarily composed of such a pair of image pick-up elements, and it is possible to properly compose the detector by one or more image pick-up elements. Moreover, the polarizing-beam splitter 13 for causing the two-dimensional photosensor arrays 14 and 15 to detect the polarization components of the interference light is also included in the "detector."

Between the beam splitter 12 and the polarizing-beam splitter 13, an aperture diaphragm and an imaging lens (lenses) are installed (not shown). The aperture diaphragm limits the beam diameter of the interference light. The imaging lens focuses (the polarization components of) the interference light to form images on the light-receiving surfaces of the two-dimensional photosensor arrays 14 and 15.

A computer 16 is provided with a controller 17, a display 18, a manipulation part 19, and a signal processor 20, as shown in FIG. 3.

The controller 17 controls each part of the optical image measurement device 1. For example, the controller 17 executes control of output of the broadband light by the light source 2, control of the reference mirror moving mechanism 9A for moving the reference mirror 9, control of the exposure times of the two-dimensional photosensor arrays 14 and 15, and control of a display process by the display 18.

The controller 17 includes a microprocessor such as a CPU, and so on. Moreover, the controller 17 includes a storage device such as a RAM, a ROM and a hard-disk drive. In the hard-disk drive, a computer program for device control is previously stored. By operation of the microprocessor according to this computer program, the controller 17 executes control of each part of the device.

Further, the controller 17 may be provided with communication equipment for performing data communication with an external device. An example of the communication equipment includes a LAN card, a modem, and the like. Thus, the controller 17 can control to acquire various types of information from an external database and register information into the database. Moreover, it is also possible to acquire information from an ophthalmic device such as an inspection device and send information to the ophthalmic device. Furthermore, the controller 17 is capable of communicating with an information system of another department and an information system of the entire hospital.

The display 18 is controlled by the controller 17 to display various kinds of information. The display 18 includes any display device such as an LCD or a CRT display.

The manipulation part 19 is used for an operator to manipulate the optical image measurement device 1 and input various information. The manipulation part 19 includes any manipulation devices and input devices, such as a mouse, a keyboard, a joystick, a trackball, or a dedicated control panel.

The signal processor 20 processes various signals. The signal processor 20 includes a microprocessor such as a CPU, and a storage device such as a RAM, a ROM and a hard-disk drive. In this storage device, a computer program for signal processing is previously stored. By making the microprocessor operate according to this computer program, the signal processor 20 performs various kinds of signal processing.

The signal processor 20 forms an image, particularly a tomographic image of the measured object 5000 according to the detection signals outputted from the two-dimensional photosensor arrays 14 and 15. This tomographic image is an image of the cross-section orthogonal to the z-direction in FIG. 1. The formation process by the signal processor 20 will be described later. The signal processor 20 is an example of the "image forming part" of the present invention.

[Operation Pattern]

An operation pattern of the optical image measurement device 1 will be described. Here, acquisition of an image of the tissue (deep tissue) of the inside of a subject body in the same manner as an endoscope will be described.

First, the controller 17 controls the light source 2 to output a broadband light. In this operation pattern, a continuous light of a broadband light is outputted.

The examiner inserts the optical fiber bundle 5 (probe) into the subject body from the top end part 5b side. At this moment, the reference mirror 9 is placed at a predetermined default position, for example. The optical image measurement device 1 acquires an image of the inside of the subject body in this state and displays the image on the display 18. For example, this image is displayed at a predetermined time interval (frame rate). While observing this image, the examiner leads the optical fiber bundle 5 near a deep tissue to be observed. The examiner may insert a conventional endoscope into the subject body and lead the optical fiber bundle 5 by referring to the endoscopic image.

Further, the examiner adjusts the position of the reference mirror 9 so that an image at a predetermined depth of a deep tissue to be observed can be obtained. For example, this process is executed by manipulation of the manipulation part 19 by the examiner and accordingly control of the reference mirror moving mechanism 9A by the controller 17. Upon completion of the positioning of the reference mirror 9, the examiner manipulates the manipulation part 19 and instructs to start acquisition of an image.

Upon receiving this instruction, the controller 17 controls the reference mirror moving mechanism 9A as necessary to set the optical path length of the reference light to a first optical path length. The first optical path length corresponds to the observation depth of the deep tissue (z-coordinate value). The controller 17 controls the exposure time of each of the two-dimensional photosensor arrays 14 and 15. The two-dimensional photosensor array 14 detects the S-polarization component of the interference light and outputs a detection signal $C_A$. The two-dimensional photosensor array 15 detects the P-polarization component of the interference light and outputs the detection signal $C_B$.

The S-polarization component and the P-polarization component of the interference light have a phase difference of 90 degrees ($\pi/2$). Accordingly, the detection signal $C_A$ and the detection signal $C_B$ have a phase difference of 90 degrees. The detection signals $C_A$ and $C_B$ can be represented by the following equations, respectively.

[Equation 1]

$$C_A(x,y) = I_s(x,y) + I_r(x,y) + \sqrt{I_s(x,y)I_r(x,y)}\cos(\Delta\phi(x,y)) \quad (1)$$

$$C_B(x,y) = I_s(x,y) + I_r(x,y) + \sqrt{I_s(x,y)I_r(x,y)}\sin(\Delta\phi(x,y)) \quad (2)$$

Here, $I_s(x,y)$ represents the intensity of the signal light and $I_r(x,y)$ represents the intensity of the reference light. Moreover, $\phi(x,y)$ represents a default phase difference. Moreover, each of the detection signals $C_A$ and $C_B$ includes background light components (incoherent components, direct-current components) $I_s(x,y)+I_r(x,y)$. Furthermore, the detection signal $C_A$ includes the interference component composed of a cos component, while the detection signal $C_B$ includes the interference component composed of a sin component.

As shown in the equations (1) and (2), each of the detection signals $C_A$ and $C_B$ uses only space (the x- and y-directions orthogonal to the z-direction) as a variable without including time as a variable. That is to say, the interference signal according to this embodiment includes only a spatial change.

Next, the controller 17 controls the reference mirror moving mechanism 9A to switch the optical path length of the reference light to a second optical path length. The second optical path length also corresponds to the site to be observed. The controller 17 controls the exposure times of the respective two-dimensional photosensor arrays 14 and 15 to output new detection signals $C_A'$ and $C_B'$.

Here, the first optical path length and the second optical path length are previously set to have a distance interval such that the detection signal $C_A$ and the detection signal $C_A'$ have a phase difference of 180 degrees ($\pi$) and the detection signal $C_B$ and the detection signal $C_B'$ have a phase difference of 180 degrees ($\pi$). Since the detection signals $C_A$ and $C_B$ have a phase difference of 90 degrees, the four detection signals $C_A$, $C_B$, $C_A'$ and $C_B'$ are obtained for every phase difference of 90 degrees.

The signal processor 20 adds the detection signals $C_A$ and $C_A'$ (phase difference: 180 degrees) and dividing the sum by two, thereby calculating the background light components $I_s$(x,y)+$I_r$(x,y). This calculation process may be performed by using the detection signals $C_B$ and $C_B'$ (phase difference: 180 degrees).

Furthermore, the signal processor 20 obtains the interference components (cos component, sin component) by subtracting the obtained background light component $I_s$(x,y)+$I_r$(x,y) from each of the detection signals $C_A$ and $C_B$. The signal processor 20 then forms an image of the cross-section in the direction orthogonal to the z-direction (lateral direction) by calculating the square sum of the interference components of the detection signals $C_A$ and $C_B$.

For example, the controller 17 controls the display 18 to display the formed image in response to the manipulation with the manipulation part 19. This image-forming process may be performed by using the detection signals $C_A'$ and $C_B'$ (phase difference: 180 degrees).

The controller 17 is capable of sequentially forming cross-sectional images at various depth positions of the deep tissue to be observed by consecutively changing the optical path length of the reference light and repeating the above process. In this process, the controller 17 controls the two-dimensional photosensor arrays 14 and 15 to output detection signals at a predetermined frame rate and at the same timing. Furthermore, the controller 17 synchronizes this frame rate, the timing to expose of the two-dimensional photosensor arrays 14 and 15, the timing to move the reference mirror 9, and the timing to change the optical path length of the reference light.

At this moment, the exposure times of the two-dimensional photosensor arrays 14 and 15 are set to be shorter than the frame rate. For example, it is possible to set the frame rate of the two-dimensional photosensor arrays 14 and 15 to 30 f/s and the exposure time to about 30-50 µs.

Further, it is also possible to acquire an image with resolution of about several µm by using a broadband light whose central wavelength is about 760 nm and wavelength width is about 100 nm. For example, in a case that a measured object is a human eye (refractive index n=1.33), assuming the wavelength of the broadband light is Gaussian type, the theoretical value of the resolution of an image to be acquired is about 1.8 µm.

The image of the deep tissue acquired in this manner is stored into any storage device such as the hard-disk drive of the controller 17.

[Actions And Effects]

The actions and effects of the optical image measurement device 1 will be described.

The optical image measurement device 1 has: the interference light generator that splits a low-coherence light (a broadband light) into a signal light and a reference light and superimposes the signal light propagated through a measured object and the reference light propagated through a reference object to generate an interference light; the two-dimensional photosensor arrays 14 and 15 that detect the interference light; and the signal processor 20 that forms an image of the measured object based on the result of the detection of the interference light.

Here, the interference light generator includes at least the light source 2, the optical fiber bundle 5, the reflector 6, the reference mirror 9, and the beam splitter 12.

The optical fiber bundle 5 is an example of the "light guiding part" of the present invention as described above. That is to say, the optical fiber bundle 5 acts to emit the signal light split from the low-coherence light from the top end part 5b and guide the signal light propagated through the measured object and entered from the top end part 5b. The interference light generator then acts to superimpose the signal light guided by the optical fiber bundle 5 and the reference light to generate an interference light.

According to the optical image measurement device 1, it is possible to place the top end part 5b near the deep tissue of the measured object 5000 by, for example, inserting the optical fiber bundle 5 into the measured object and perform a measurement.

Furthermore, according to the optical image measurement device 1, it is possible to form an image of the deep tissue with µm-level resolution by employing the OCT technology.

Thus, according to the optical image measurement device 1, it is possible to image the microstructure of the deep tissue of the measured object.

Further, by using the optical fiber bundle 5 having flexibility, it is possible to favorably insert the optical fiber bundle 5 into the measured object, for example. Specifically, in a case that a path from the opening on the surface of the measured object to the deep tissue is bent, it is possible to favorably lead the optical fiber bundle 5 near the deep tissue.

Further, the optical fiber bundle 5 is provided with the reflector 6 that splits the low-coherence light entered from the base end part 5a into the signal light and the reference light. The signal light is then emitted from the top end part 5b, propagated through the measured object, entered into the optical fiber bundle 5 from the top end part 5b, guided to the base end part 5a, and emitted. On the other hand, the reference light is emitted from the base end part 5a. The signal light and the reference light emitted from the base end part 5a, respectively, are superimposed with each other to become an interference light.

Thus, by sharing part of the optical path of the signal light and part of the optical path of the reference light, it is possible to shorten the optical path of the reference light alone, and it is possible to simplify the device configuration. In the optical image measurement device utilizing the OCT technology, unlike a device such as an endoscope and a confocal microscope, it is necessary to match the optical path length of the signal light with that of the reference light to generate an interference light. However, with the configuration as in this embodiment, this requirement may be favorably satisfied.

Of the optical path of the reference light alone, the length of the optical path between the beam splitter 7 and the reference mirror 9 is matched with the length between the reflector 6 and the depth position to be observed of the measured object

5000. That is to say, by moving the reference mirror 9 to change the abovementioned optical path length, it is possible to change the depth position to be observed (the z-coordination value).

The term "optical path length (length of the optical path)" refers to not only the length of the optical path in the spatial distance but also the length of the optical path in the optical distance considering the refractive index and placement of the optical member.

[Modification]

A modification of the full-field optical image measurement device will be described.

In the above embodiment, the optical image measurement device 1 that detects polarization components of the interference light has been described. However, the full-field optical image measurement device is not limited to the above type. For example, as described in Japanese Unexamined Patent Application Publication No. 2001-330558, it is possible to apply a configuration that extracts different phase components of the interference light by using an opto-isolator (shutter).

However, the advantage of the type utilizing the polarization property as in the above embodiment is that neither complicated components, such as a shutter, nor precise control of the shutter are necessary. Further, according to the type utilizing the polarization property, the four components ($C_A$, $C_B$, $C_A'$, $C_B'$) required for forming an image can be acquired by two measurements, which provides the advantage of allowing for shortened measurement time (for some other types, measurements should be repeated three times or more).

In the above embodiment, in a case that the optical fiber bundle 5 is long or in a case that the reflector 6 is disposed closer to the base end part 5a, it may be necessary to elongate the optical path length of the reference light alone. In such cases, it is possible to dispose an optical member that extends the optical path length of the reference light. This optical member is disposed on the optical path of the reference light alone, for example, between the beam splitter 7 and the reference mirror 9. This makes it possible to generate an interference light while maintaining information included in the signal light. This optical element is made of a material with a large refractive index, for example. This optical element is an example of the optical member for matching the optical path length of the signal light with that of the reference light.

Some optical elements, such as a prism and a lens, disperse light. When the influence of dispersion applied to the signal light is different from that applied to the reference light, the interference position of the signal light and the reference light may vary depending on wavelength components, and therefore, there is a fear that a favorable interference light cannot be obtained. In order to prevent such a situation, it is possible to dispose an optical member for matching the influence of dispersion applied to the signal light with that applied to the reference light. As this optical member, for example, a prism member such as a pair prism, a liquid cell that encapsulates liquid such as water, a glass block, or the like can be used.

It is desirable that the optical member for matching the optical path length and the influence of dispersion is disposed on the optical path of the reference light alone, for example, between the beam splitter 7 and the reference mirror 9, in order to maintain the information included in the signal light.

The optical system employed in the above optical image measurement device 1 is only an example of the optical system of the full-field optical image measurement device. For example, it is possible to employ any interferometer, such as the Michelson type and the Mach-Zehnder type.

Figure 4:
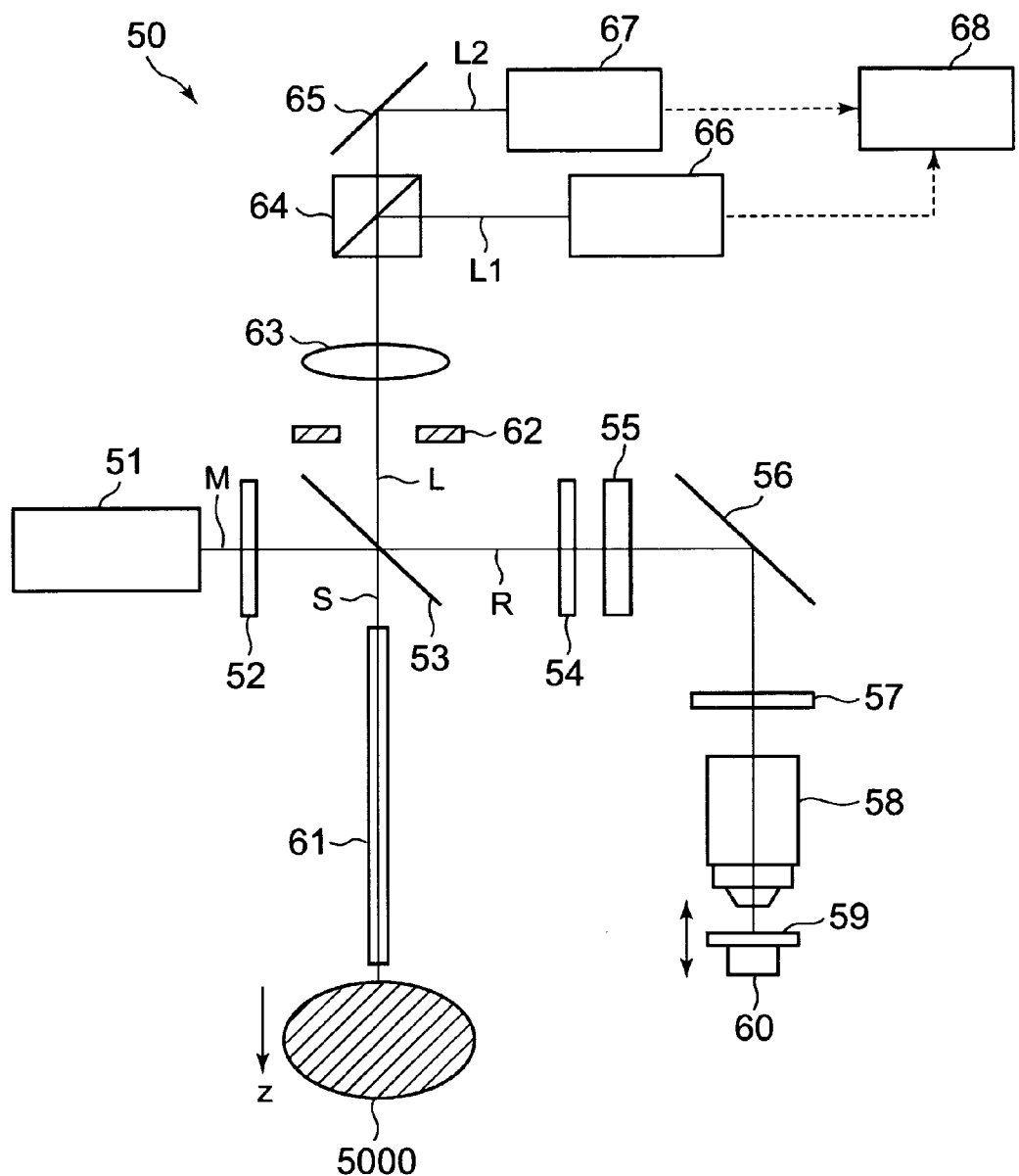
FIG. 4 is a schematic view illustrating an example of the configuration of a modification of the first embodiment of the optical image measurement device according to the present invention.

Here, an optical image measurement device that employs a Michelson-type interferometer will be described. An optical image measurement device 50 shown in FIG. 4 is an example of such an optical image measurement device.

The optical image measurement device 50 is provided with a halogen lamp 51 as a light source. The halogen lamp 51 outputs a non-polarized broadband light M, for example. Although the illustration is omitted, the halogen lamp 51 can be configured to include an optical fiber bundle that guides an output light and a Kohler illumination optical system for uniformly illuminating the radiation field of the output light, together with a general halogen lamp. The non-polarized broadband light M outputted from the halogen lamp 51 has a predetermined beam diameter.

The light source is not limited to the halogen lamp 51 and may be any light source that outputs a non-polarized broadband light. For example, any thermal light source, such as a xenon lamp, can be applied. Further, the light source may be a laser light source that outputs a randomly-polarized broadband light. Hereinafter, a case of non-polarized light will be described in detail.

The broadband light M outputted by the halogen lamp 51 includes light of various bands. A filter 52 is a filter that transmits only a predetermined band of the non-polarized broadband light M. The predetermined band to be transmitted is determined by the resolution, the measurement depth or the like, and is set to, for example, a band whose central wavelength is about 760 nm and whose wavelength width is about 100 nm. The light transmitted through the filter 52 is referred to as the broadband light M as well.

The non-polarized broadband light M transmitted through the filter 52 is split into two by a beam splitter 53, such as a half mirror. That is to say, the reflected light from the beam splitter 53 forms the signal light S and the light transmitted through the beam splitter 53 forms the reference light R.

The non-polarized reference light R generated by the beam splitter 53 is passed through a waveplate ($\lambda/4$ plate) 54 and a polarizing plate 55, and reflected by a reflection mirror 56. Furthermore, the reference light R is passed through a glass plate 57, and focused on the reflection surface of a reference mirror 59 by an objective lens 58. The reference light R reflected by the reference mirror 59 is propagated on the same optical path reversely, and returns to the beam splitter 53.

At this moment, the reference light R having been initially non-polarized is converted into a circularly-polarized light by being propagated through the waveplate 54 and the polarizing plate 55 twice. The glass plate 57 is an optical member for matching the influences of dispersion that occur on the optical paths of the signal light S and reference light R (both the arms of interferometer), respectively.

The reference mirror 59 is configured to be movable in the traveling direction of the reference light R, that is, in the direction orthogonal to the reflection surface of the reference mirror 59 (the direction of an arrow pointing to both the sides in FIG. 4) by the reference mirror moving mechanism 60. The reference mirror moving mechanism 60 includes a driver such as a piezo element.

By thus moving the reference mirror 59, the difference in optical path length of the signal light S and the reference light R is changed. Here, the optical path length of the signal light S is a to-and-from distance between the beam splitter 53 and the depth position to be observed of the measured object 5000. Further, the optical path length of the reference light R is determined a to-and-from distance between the beam splitter 53 and the reflection surface of the reference mirror 59. By changing the difference in optical path length between the signal light S and the reference light R, it is possible to selectively acquire images at various depth positions of the measured object 5000.

In this embodiment, the difference in optical path length is changed by changing the optical path length of the reference light R; however, it is also possible to use a configuration in which the abovementioned difference in optical path length is changed by changing the optical path length of the signal light S. In this case, a configuration that changes the interval between the device optical system and a measured object is provided. Specifically, for example, a stage that moves the device optical system in the z-direction and a stage that moves the measured object 5000 in the z-direction can be applied.

The signal light S enters an optical fiber bundle 61 while maintaining the non-polarized state. In such a case that the beam diameter of the signal light S is larger than the diameter of the optical fiber bundle, an optical element such as a converging lens for decreasing the beam diameter of the signal light S may be placed between the beam splitter 53 and the optical fiber bundle 61.

The optical fiber bundle 61 has a similar configuration to that of the optical fiber bundle 5 of the above embodiment. The optical fiber bundle 61 of this modification is not provided with the reflecting part or splitter such as the reflector 6 in the above embodiment. To the top end part of each of the optical fibers composing the optical fiber bundle 61 (the end part on the measured object 5000 side), a microlens is disposed as in the above embodiment (refer to FIG. 2). The signal light S guided by each optical fiber is focused by this microlens at the depth position to be observed of the measured object 5000.

The signal light S radiated by the measured object 5000 is reflected and scattered on the surface and the inside of the measured object 5000, and enters the optical fiber bundle 61 from the abovementioned top end part. Furthermore, the signal light S is guided by the optical fiber bundle 61, exits from the base end part (the end part on the opposite side of the abovementioned top end part), and returns to the beam splitter 53.

The signal light S propagated through the measured object 5000 and the reference light R propagated through the reference mirror 59 are superimposed by the beam splitter 53, and the interference light L is generated. The interference light L includes an S-polarization component and a P-polarization component. The interferometer including the halogen lamp 51, the beam splitter 53 and the reference mirror 59 is an example of the "interference light generator" of the present invention.

The interference light L generated by the beam splitter 53 travels through an aperture diaphragm 62 and is converged by an imaging lens (lenses) 63 to become a converged light. The S-polarization component L1 of the interference light L that has become a converged light is reflected by a polarizing-beam splitter 64 and detected by a CCD (image sensor) 66. On the other hand, the P-polarization component L2 of the interference light L is transmitted through the polarizing-beam splitter 64, reflected by a reflection mirror 65, and detected by a CCD (image sensor) 67.

Each of the CCDs 66 and 67 has a two-dimensional light-receiving surface. The S-polarization component L1 and the P-polarization component L2 are radiated to the light-receiving surfaces of the CCDs 66 and 67 with certain beam diameters, respectively.

The CCDs 66 and 67 having detected the S-polarization component L1 and the P-polarization component L2, respectively, send detection signals to the computer 68, respectively. The CCDs 66 and 67 are examples of the "detector" of the present invention. A two-dimensional photosensor array other than the CCD may be used as the detector.

Since the reference light R and the signal light S are, respectively, a circularly-polarized light and a non-polarized light that compose the interference light L, the S-polarization component L1 and the P-polarization component L2 have a phase difference of 90 degrees ($\pi/2$). Accordingly, a detection signal $D_A$ outputted from the CCD 66 and a detection signal $D_B$ outputted from the CCD 67 have a phase difference of 90 degrees. Therefore, these detection signals may be represented by the equations (1) and (2) described before.

As in the above embodiment, the computer 68 controls the reference mirror moving mechanism 60 to switch the optical path length of the reference light R and executes a new measurement in that state. Consequently, the CCDs 66 and 67 output new detection signals $D_A'$ and $D_B'$.

Here, the optical path length of the reference light R in the first measurement and the optical path length of the reference light R in the next measurement are previously set to have a distance interval such that the detection signal $D_A$ and the detection signal $D_A'$ have a phase difference of 180 degrees ($\pi$) and the detection signal $D_B$ and the detection signal $D_B'$ have a phase difference of 180 degrees ($\pi$). Since the detection signals $D_A$ and $D_B$ have a phase difference of 90 degrees, the four detection signals $D_A$, $D_B$, $D_A'$ and $D_B'$ are obtained for every phase difference of 90 degrees.

The computer 68 calculates the background light component $I_s(x,y)+I_r(x,y)$ by adding the detection signals $D_A$ and $D_A'$ (phase difference: 180 degrees) and dividing the sum by two. This calculation process may be executed by using the detection signals $D_B$ and $D_B'$ (phase difference: 180 degree).

Furthermore, the computer 68 obtains the interference components (cos component, sin component) by subtracting the obtained background light component $I_s(x,y)+I_r(x,y)$ from the respective detection signals $D_A$ and $D_B$. The computer 68 then calculates a square sum of the interference components of the detection signals $D_A$ and $D_B$ to form a tomographic image having a cross-section in a direction orthogonal to the z direction (the xy direction, the lateral direction).

The computer 68 displays the formed tomographic image. The computer 68 has a similar configuration to the computer 16 in the above described embodiment (refer to FIG. 3).

According to the optical image measurement device 50 to which such a Michelson-type interferometer is applied, it is possible to execute a measurement by placing the top end part near the deep tissue of the measured object 5000, for example, inserting the optical fiber bundle 61 into the measured object.

Furthermore, according to the optical image measurement device 50, it is possible to form an image of the deep tissue at µm-level resolution by using the OCT technology.

Thus, according to the optical image measurement device 50, it is possible to image the microstructure of the deep tissue of the measured object.

Further, it is possible to use flexible fibers as the optical fiber bundle 61. This makes it possible to favorably insert the optical fiber bundle 61 into a subject, for example. Specifically, in a case that the path from the opening on the surface to the deep tissue of the subject is bent, it is possible to favorably lead the optical fiber bundle 61 near the deep tissue.

Second Embodiment

An application example of the present invention to the Fourier-domain type and swept-source type optical image measurement devices will be described.

[Device Configuration]

Figure 5:
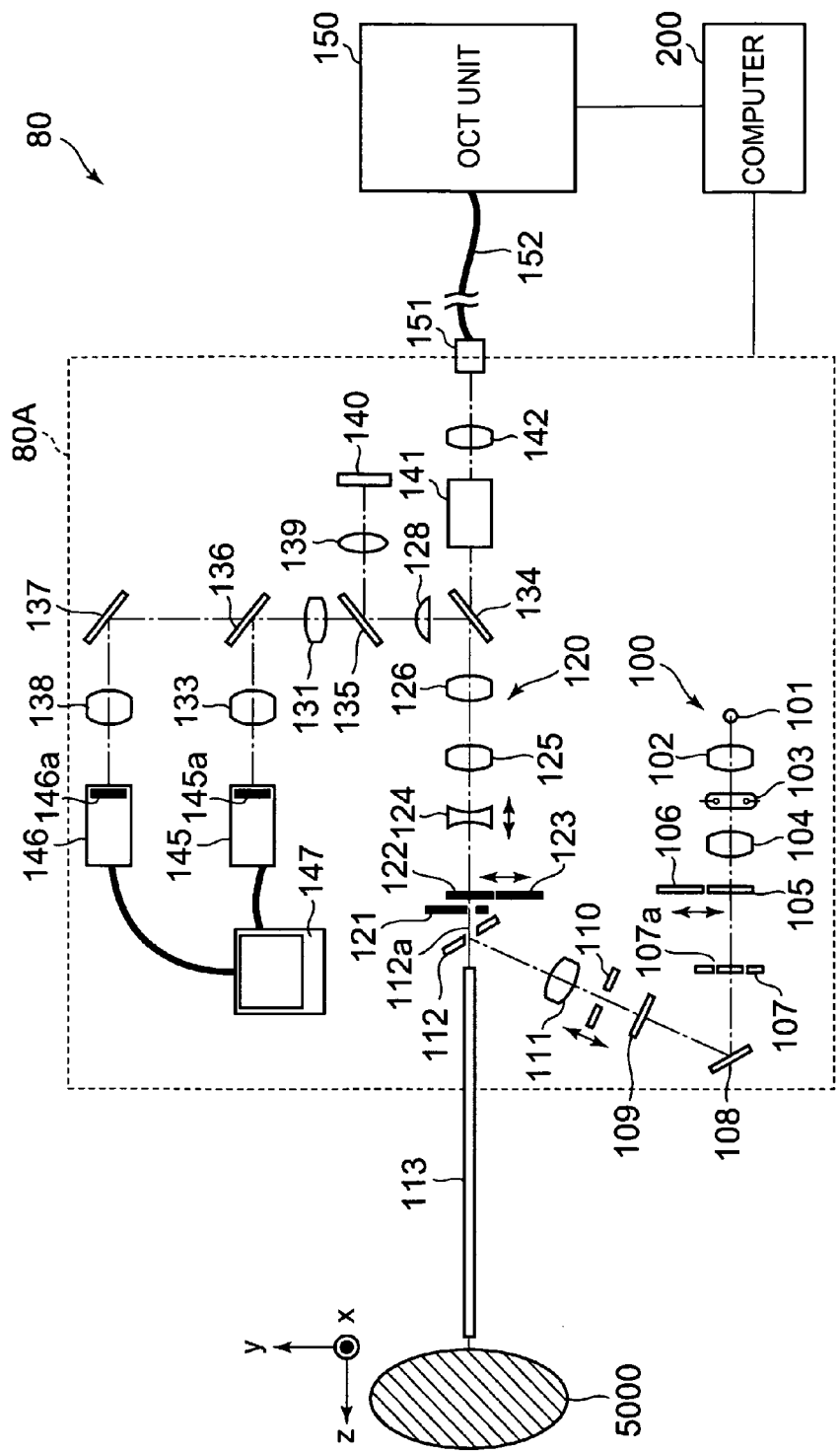
FIG. 5 is a schematic view illustrating an example of the configuration of a second embodiment of the optical image measurement device according to the present invention.

An optical image measurement device 80 shown in FIG. 5 is a device capable of capturing a tomographic image of the measured object 5000 by utilizing the OCT technology and capturing an image of the surface of the measured object 5000. The optical image measurement device 80 is a device for capturing an image of a deep tissue in a subject body, such as the fundus oculi and an internal organ. In this embodiment, a case that the measured object 5000 is the fundus oculi will be described.

The optical image measurement device 80 includes an optical system unit 80A, an OCT unit 150 and a computer 200 as shown in FIG. 5. The optical system unit 80A has an optical system for capturing a two-dimensional image of the surface of the measured object 5000. Since the measured object 5000 is the fundus oculi, the optical system unit 80A is configured substantially similarly to a conventional retinal camera. The OCT unit 150 stores an optical system for capturing an image by utilizing the OCT technology. The computer 200 is provided with a computer that executes various kinds of calculation processes, control processes and so on.

To the OCT unit 150, one end of a connecting line 152 is attached. To the other end of the connecting line 152, a connector part 151 that connects the connecting line 152 to the optical system unit 80A is attached. An optical fiber runs through the inside of the connecting line 152. Thus, the OCT unit 150 and the optical system unit 80A are optically connected via the connecting line 152.

[Configuration of Optical System Unit]

The optical system unit 80A is used for forming a two-dimensional image of the surface of the measured object 5000 based on the optically acquired data (data detected by imaging device 145 and 146).

Here, a two-dimensional image of the surface of the measured object 5000 represents a color image and a monochrome image of the surface of the measured object 5000. Furthermore, a fluorescence image of the fundus oculi as the measured object 5000 (a fluorescein fluorescence image, an indocyanine green fluorescence image, or the like) is also included in the two-dimensional image. Similarly to a conventional retinal camera, the optical system unit 80A is provided with an illumination optical system 100 that illuminates the measured object 5000 and an imaging optical system 120 that guides the fundus oculi reflected light of this illumination light to the imaging device 145 and 146.

The imaging device 145 detects an illumination light having a wavelength of the near-infrared region. Further, the imaging device 146 detects an illumination light having a wavelength of the visible region. Furthermore, the imaging optical system 120 acts to guide the signal light from the OCT unit 150 to the measured object 5000 and also guide the signal light propagated through the measured object 5000 to the OCT unit 150.

The illumination optical system 100 includes an observation light source 101, a condenser lens 102, an imaging light source 103, a condenser lens 104, exciter filters 105 and 106, a ring translucent plate 107, a mirror 108, an LCD (Liquid Crystal Display) 109, an illumination diaphragm 110, a relay lens 111, an aperture mirror 112, and an optical fiber bundle 113.

The observation light source 101 outputs an illumination light having a wavelength of the visible region included in a range of, for example, about 400-700 nm. Further, the imaging light source 103 outputs an illumination light having a wavelength of the near-infrared region included in a range of, for example, about 700-800 nm. The near-infrared light outputted from the imaging light source 103 is set to have a wavelength shorter than the wavelength of the light used in the OCT unit 150.

The optical fiber bundle 113 has a configuration similar to that of the optical fiber bundle 5 of the first embodiment described above (refer to FIG. 2). That is to say, the optical fiber bundle 113 is configured by bundling a plurality of optical fibers, and a microlens is disposed to the top end part of each of the optical fibers (the end part on the measured object 5000 side). This optical fiber bundle 113 is not provided with a splitter or a reflecting part such as the reflector 6 of FIG. 1.

The imaging optical system 120 includes an optical fiber bundle 113, an (aperture 112a of an) aperture mirror 112, an imaging diaphragm 121, barrier filters 122 and 123, a variable magnification lens 124, a relay lens 125, an imaging lens 126, a dichroic mirror 134, a field lens 128, a half mirror 135, a relay lens 131, a dichroic mirror 136, an imaging lens 133, an imaging device 145 (an image pick-up element 145a), a reflection mirror 137, an imaging lens 138, an imaging device 146 (an image pick-up element 146a), a lens 139, and an LCD 140.

Furthermore, the imaging optical system 120 is provided with a dichroic mirror 134, a half mirror 135, a dichroic mirror 136, a reflection mirror 137, an imaging lens 138, a lens 139, and an LCD 140.

The dichroic mirror 134 is configured to reflect the fundus oculi reflected light of the illumination light from the illumination optical system 100 (having a wavelength included in the range of about 400-800 nm) and transmit the signal light LS from the OCT unit 150 (for example, having a wavelength included in the range of about 800-900 nm; described later).

Further, the dichroic mirror 136 is configured to transmit the illumination light having a wavelength of the visible region from the illumination optical system 100 (a visible light having a wavelength of about 400-700 nm outputted from the observation light source 101) and reflect the illumination light having a wavelength of the near-infrared region (a near-infrared light having a wavelength of about 700-800 nm outputted from the imaging light source 103).

The LCD 140 displays a fixation target (an internal fixation target) for fixing an eye. The light from the LCD 140 is focused by the lens 139 and thereafter reflected by the half mirror 135, travels through the field lens 128, and is reflected by the dichroic mirror 136. Furthermore, this light travels through the imaging lens 126, the relay lens 125, the variable magnification lens 124, the aperture mirror 112 (the aperture 112a), the optical fiber bundle 113 and so on, and enters the eye. The internal fixation target is thereby projected onto the measured object 5000 of the eye.

The image pick-up element 145a is an image pick-up element such as a CCD or a CMOS built into an imaging device 145 such as a television camera, and specifically detects light having a wavelength of the near-infrared region. That is to say, the imaging device 145 is an infrared television camera that detects near-infrared light. The imaging device 145 outputs a video signal as the result of detection of the near-infrared light.

The touch-panel monitor 147 displays a two-dimensional image (a fundus oculi image) of the surface of the measured object 5000 based on this video signal. Further, this video signal is sent to the computer 200, and the fundus oculi image is displayed on the display.

At the time of capture of an image by the imaging device 145, an illumination light having a wavelength of the near-infrared region outputted from the imaging light source 103, for example, is used.

On the other hand, the image pick-up element 146a is an image pick-up element, such as a CCD or CMOS, built into the imaging device 146, such as a television camera, and specifically detects the light with a wavelength of the visible region. That is to say, the imaging device 146 is a television camera that detects a visible light. The imaging device 146 outputs a video signal as a result of detecting the visible light.

The touch-panel monitor 147 displays a two-dimensional image (a fundus oculi image) of the surface of the measured object 5000 based on this video signal. Further, this video signal is sent to the computer 200, and the fundus oculi image is displayed on the display.

At the time of capture of an image by the imaging device 146, an illumination light having a wavelength of the visible region outputted from the observation light source 101 of the illumination optical system 100, for example, is used.

The optical system unit 80A is provided with a scan unit 141 and a lens 142. The scan unit 141 is provided with a configuration for scanning the radiation position of the light outputted from the OCT unit 150 (signal light LS; described later) to the measured object 5000.

As described in the first embodiment (refer to FIG. 2), a plurality of optical fibers are placed in the optical fiber bundle 113. The scan unit 141 scans the radiation position of the signal light LS to the measured object 5000 by making the signal light LS sequentially enter the plurality of optical fibers.

The lens 142 collimates the signal light LS guided from the OCT unit 150 through the connecting line 152 and makes the light enter the scan unit 141. Further, the lens 142 focuses the fundus oculi reflected light of the signal light LS propagated through the scan unit 141.

Figure 6:
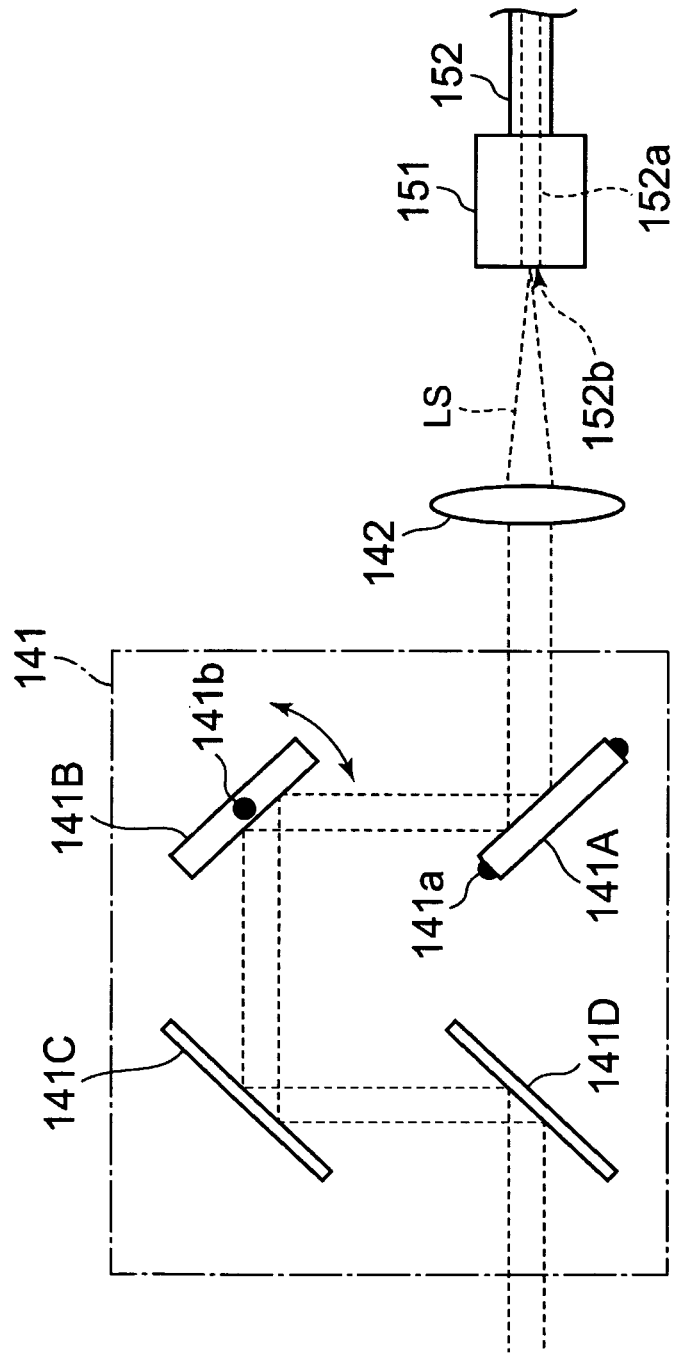
FIG. 6 is a schematic view illustrating an example of the configuration of the second embodiment of the optical image measurement device according to the present invention.

FIG. 6 shows an example of the configuration of the scan unit 141. The scan unit 141 includes Galvano mirrors 141A, 141B and reflection mirrors 141C, 141D.

The Galvano mirrors 141A and 141B are reflection mirrors disposed so as to be rotatable about rotary axes 141a and 141b, respectively. The respective Galvano mirrors 141A and 141B are rotated about the rotary axes 141a and 141b, respectively, by a drive mechanism (not shown). Consequently, the direction of the reflection surface (surface that reflects the signal light LS) of each of the Galvano mirrors 141A and 141B is changed.

The rotary axes 141a and 141b are placed orthogonally to each other. In FIG. 6, the rotary axis 141a of the Galvano mirror 141A is placed in a direction parallel to the paper surface. Further, the rotary axis 141b of the Galvano mirror 141B is placed in a direction orthogonal to the paper surface.

That is to say, the Galvano mirror 141B is configured to be rotatable in the direction shown by an arrow pointing to both the sides in FIG. 6, while the Galvano mirror 141A is configured to be rotatable in the direction orthogonal to the arrow pointing to both the sides. The Galvano mirrors 141A and 141B thereby act to change the reflecting direction of the signal light LS to mutually orthogonal directions. As seen from FIG. 5 and FIG. 6, when the Galvano mirror 141A is rotated, a scan with the signal light LS is executed in the x-direction, and when the Galvano mirror 141B is rotated, a scan with the signal light LS is executed in the y-direction.

The signal light LS reflected by the Galvano mirrors 141A and 141B is reflected by the reflection mirrors 141C and 141D, and travels in the same direction when entering the Galvano mirror 141A.

An end surface 152b of the optical fiber 152a inside the connecting line 152 is placed so as to face the lens 142. The signal light LS emitted from the end surface 152b travels toward the lens 142 while increasing the beam diameter thereof, and is collimated by the lens 142. Conversely, the signal light LS propagated through the measured object 5000 is focused toward the end surface 152b by the lens 142, and enters the optical fiber 152a.

[Configuration of OCT Unit]

Next, the configuration of the OCT unit 150 will be described with reference to FIG. 7. The OCT unit 150 is a device for forming a tomographic image of the measured object 5000 based on the optically acquired data (data detected by the CCD 184; described later). This tomographic image is a tomographic image at the cross-section including the z-direction.

The OCT unit 150 is provided with an optical system substantially similar to that of the conventional Fourier-domain type optical image measurement device. That is to say, the OCT unit 150 splits the low-coherence light into the reference light and the signal light, superimposes the signal light propagated through a measured object and the reference light propagated through the reference object to generate an interference light, and detects this light. The result of this detection (a detection signal) is inputted into the computer 200. The computer 200 analyzes this detection signal to form a tomographic image of the measured object.

A low-coherence light source 160 is composed of a broadband light source that outputs a low-coherence light L0, such as a Super Luminescent Diode (SLD) or a Light-Emitting Diode (LED). As the low-coherence light L0, for example, a light including a light a wavelength of the near-infrared region and a light having a temporal coherence length of several tens of micrometers is used.

The low-coherence light L0 has a wavelength longer than the illumination light of the optical system unit 80A (wavelength: about 400 nm to 800 nm), for example, a wavelength included in the range of about 800 nm to 900 nm.

The low-coherence light L0 outputted from the low-coherence light source 160 is guided to an optical coupler 162 through an optical fiber 161. The optical fiber 161 is composed of, for example, a single mode fiber or a PM fiber (Polarization Maintaining fiber). The optical coupler 162 splits the low-coherence light L0 into the reference light LR and the signal light LS.

Although the optical coupler 162 acts as both a light splitter (a splitter) and a light superimposing means (a coupler), it will be herein referred to as an "optical coupler" generically.

The reference light LR generated by the optical coupler 162 is guided by an optical fiber 163 composed of a single mode fiber or the like, and emitted from the fiber end surface. Furthermore, the reference light LR is collimated by a collimator lens 171 and thereafter propagated through an optical fiber (bundle) and a density filter 173, and reflected by the reference mirror 174. The reference mirror 174 is an example of the "reference object" of the present invention.

The reference light LR reflected by the reference mirror 174 again travels through the density filter 173 and the optical fiber 172, is focused on the fiber end surface of the optical fiber 163 by the collimator lens 171, and is guided through the optical fiber 163 to the optical coupler 162.

Here, the optical fiber 172 and the density filter 173 act as an optical member for matching the optical path lengths (optical distances) of the reference light LR and the signal light LS and as an optical member for matching the influences of dispersion applied to the reference light LR and the signal light LS, respectively.

Further, the density filter 173 also acts as a neutral density filter that reduces the light amount of the reference light and is composed of a rotary-type ND (Neutral Density) filter, for example. The density filter 173 is driven to rotate by a drive mechanism (not shown) including a driving device such as a motor, thereby changing the reduction amount of the light amount of the reference light LR. Consequently, it is possible to change the light amount of the reference light LR that contributes to generation of the interference light LC.

Figure 7:
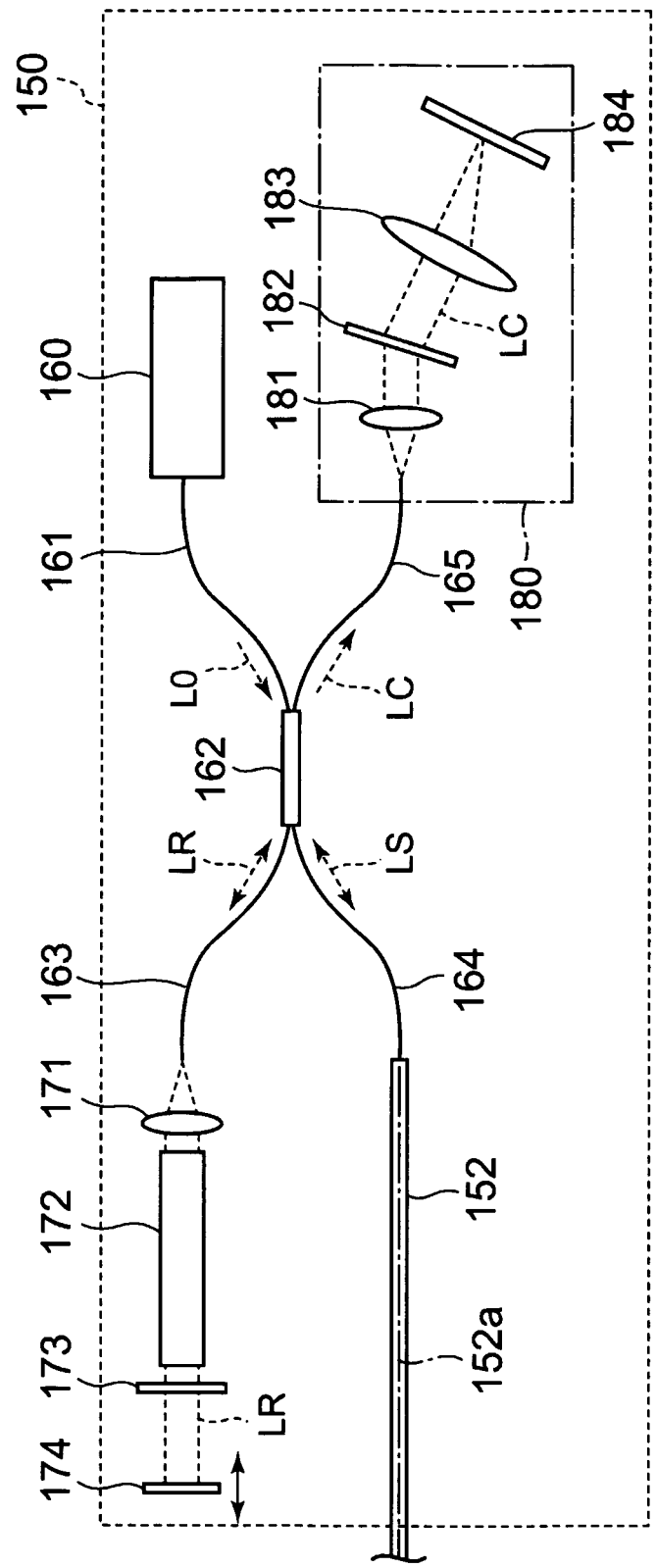
FIG. 7 is a schematic view illustrating an example of the configuration of the second embodiment of the optical image measurement device according to the present invention.

Further, the reference mirror 174 is moved in the traveling direction of the reference light LR (a direction of an arrow pointing to both sides in FIG. 7). Consequently, it is possible to ensure the optical path length of the reference light LR corresponding to the axial length of the eye or the like. Moreover, by moving the reference mirror 174, it is possible to acquire an image at any depth position of the measured object 5000. The reference mirror 174 is moved by a drive mechanism (not shown) including a driving device such as a motor.

On the other hand, the signal light LS generated by the optical coupler 162 is guided to the end part of the connecting line 152 by the optical fiber 164 composed of a single mode fiber or the like. The optical fiber 152*a* runs through the inside of the connecting line 152. The optical fiber 164 and the optical fiber 152*a* may be formed by a single optical fiber, or may be integrally formed by, for example, joining the respective end surfaces. In any case, it is sufficient if the optical fibers 164 and 152*a* are configured to be capable of transmitting the signal light LS between the optical system unit 80A and the OCT unit 150.

The signal light LS is guided through the inside of the connecting line 152 and led to the optical system unit 80A. Furthermore, the signal light LS travels through the lens 142, the scan unit 141, the dichroic mirror 134, the imaging lens 126, the relay lens 125, the variable magnification lens 124, the imaging diaphragm 121, and the aperture part 112*a* of the aperture opening mirror 112, and enters the optical fiber bundle 113. At this moment, a scan with the signal light LS is executed by the scan unit 141 so as to enter a certain optical fiber (one or more optical fibers) of the optical fiber bundle 113. Then, the signal light LS is guided by this optical fiber, emitted from the top end part thereof, and radiated to the measured object 5000. When radiating the signal light LS to the measured object 5000 (the fundus oculi), the barrier filters 122 and 123 are retracted from the optical path in advance.

The signal light LS having entered the measured object 5000 forms an image at a depth position to be observed of the measured object 5000, and is reflected. At this moment, the signal light LS is reflected and scattered on the surface of the measured object 5000 and at the border of the refractive index of the deep region. Therefore, the signal light LS propagated through the measured object 5000 includes information that reflects a backscatter condition at the border of the refractive index around the depth position to be measured. This light may be simply referred to as the "fundus oculi reflected light of the signal light LS."

The fundus oculi reflected light of the signal light LS reversely travels on the abovementioned path in the optical system unit 80A to be focused on the end surface 152*b* of the optical fiber 152*a*, enters the OCT unit 150 through the optical fiber 152, and returns to the optical coupler 162 through the optical fiber 164.

The optical coupler 162 superimposes the signal light LS propagated through the measured object 5000 and the reference light LR propagated through the reference mirror 174 to generate the interference light LC. The generated interference light LC is guided to the spectrometer 180 through the optical fiber 165 composed of a single mode fiber or the like.

Although a Michelson-type interferometer is employed in this embodiment, it is possible to employ any type of interferometer such as the Mach-Zehnder type as necessary.

The "interference light generator" of the present invention includes the optical coupler 162, an optical member on the optical path of the signal light LS (that is, an optical member placed between the optical coupler 162 and the measured object 5000), and an optical member on the optical path of the reference light LR (that is, an optical member placed between the optical coupler 162 and the reference mirror 174), for example. Specifically, the interference light generator includes the optical coupler 162, the optical fibers 163 and 164, the reference mirror 174, and the optical fiber bundle 113.

The spectrometer 180 includes a collimator lens 181, a diffraction grating 182, an imaging lens 183, and a CCD 184. The diffraction grating 182 may be a transmissive-type diffraction grating that transmits light, or may be a reflective-type diffraction grating that reflects light. Further, instead of the CCD 184, it is possible to use another photodetector element such as a CMOS.

The interference light LC having entered the spectrometer 180 is paralleled by the collimator lens 181, and is divided by the diffraction grating 182 (spectral resolution). The divided interference light LC forms an image on the imaging surface of the CCD 184 by the imaging lens 183. The CCD 184 detects each spectrum of the divided interference light LC to convert into an electrical signal, and outputs this detection signal to the computer 200. The CCD 184 is an example of the "detector" of the present invention.

[Configuration of Computer]

Next, the configuration of the computer 200 will be described. The computer 200 analyzes the detection signal inputted from the CCD 184 of the OCT unit 150, and forms a tomographic image of the measured object 5000. The analysis method in this process is similar to that in a conventional Fourier-domain OCT.

Further, the computer 200 forms a two-dimensional image representing the morphology of the surface of the measured object 5000 based on the video signals outputted from the imaging devices 145 and 146 of the optical system unit 80A. This two-dimensional image may be a still image or a motion image. The computer 200 executes control of the light sources 101 and 103 and the imaging devices 145 and 12 to acquire these images.

The computer 200 controls each part of the optical system unit 80A and the OCT unit 150.

As controls of the optical system unit 80A, the computer 200 executes, for example: control of output of the illumination light by the observation light source 101 and the imaging light source 103; control of the inserting/retracting operations to/from the optical path of the exciter filters 105, 106 and the barrier filters 122, 123; control of the operation of a display device such as the LCD 140; control of movement of the illumination diaphragm 110 (control of the aperture value); control of the aperture value of the imaging diaphragm 121; control of movement of the variable magnification lens 124 (control of magnification). Furthermore, the computer 200 executes control of the operations of the Galvano mirrors 141A and 141B.

Further, as controls of the OCT unit 150, the computer 200 executes, for example: control of output of the low-coherence light L0 by the low-coherence light source 160; control of movement of the reference mirror 174; control of the rotation operation of the density filter 173 (the operation of changing the reduction amount of the light amount of the reference light LR); and control of the accumulation time of the CCD 184.

Similarly to a conventional computer, the computer 200 includes a microprocessor, a RAM, a ROM, a hard-disk drive, a keyboard, a mouse, a display, a communication interface (1/F), and so on. Further, the computer 200 is provided with an image forming board for forming a tomographic image of the measured object 5000.

[Operation Pattern]

An example of the operation pattern of the optical image measurement device 80 according to this embodiment will be described.

Capture of a two-dimensional image of the surface of the measured object 5000 (a fundus oculi image) is executed as in a conventional retinal camera. The optical image measurement device 80 is similar to a conventional retinal camera except that an illumination light for capturing a fundus oculi image is illuminated on the fundus oculi via the optical fiber bundle 113. When capturing a fundus oculi image, it is possible to retract the optical fiber bundle 113 from the optical path and place an objective lens on the optical path instead. In this case, it is possible to capture a fundus oculi image as in a conventional retinal camera.

A measurement of an image with the OCT technology will be described below. Here, the number of the optical fibers included in the optical fiber bundle 113 is denoted by M.

First, the computer 200 controls the scan unit 141 so that the signal light LS enters a first optical fiber of the optical fiber bundle 113, and turns the low-coherence light source 160 on. Consequently, a first interference light LC based on the signal light LS propagated through a position (a first position) of the measured object 5000 corresponding to the first optical fiber and the reference light LR is detected.

The computer 200 forms an image along the depth direction (z-direction) at the first position, based on the first interference light LC.

Since the position of each optical fiber is constant, the positions of the Galvano mirrors 141A and 141B for making the signal light LS enter the first optical fiber can be previously determined. The computer 200 previously stores these positions of the Galvano mirrors 141A and 141B (the same as described above hereinafter).

Next, the computer 200 controls the scan unit 141 so that the signal light LS enters a second optical fiber and turns the low-coherence light source 160 on. Consequently, a second interference light LC based on the signal light LS propagated through a position (a second position) of the measured object 5000 corresponding to the second optical fiber and the reference light LR is detected.

The computer 200 forms an image along the depth direction at the second position, based on this second interference light LC.

Thus, the optical image measurement device 80 sequentially makes the signal light LS enter the M-pieces of optical fibers to execute measurements, and sequentially forms images along the depth direction at the first to Mth positions. The computer 200 forms a tomographic image of the measured object 5000 based on these M-pieces of images along the depth direction. At this moment, the computer 200 forms a tomographic image by arranging the images along the depth direction in accordance with arrangement information of the M-pieces of optical fibers (previously stored).

[Actions and Effects]

The actions and effects of the optical image measurement device 80 will be described.

The optical image measurement device 80 is provided with: the interference light generator that splits the low-coherence light into the signal light and the reference light, and superimposes the signal light propagated through the measured object and the reference light propagated through the reference object to generate an interference light; the CCD 184 that detects the interference light; and the computer 200 that forms an image of the measured object based on the detection result of the interference light.

The optical fiber bundle 113 is an example of the "light guiding part" of the present invention. That is to say, the optical fiber bundle 113 acts to emit the signal light split from the low-coherence light from the top end part and to guide the signal light having entered from the top end part through the measured object. Then, the interference light generator acts to superimpose the signal light guided by the optical fiber bundle 113 and the reference light to generate the interference light.

According to the optical image measurement device 80, it is possible to execute a measurement by placing the top end part of the optical fiber bundle 113 near a deep tissue of the measured object 5000 by, for example, inserting the optical fiber bundle 113 into a subject body.

Furthermore, according to the optical image measurement device 80, it is possible to form an image with the μm-level resolution of a deep tissue by using the OCT technology.

Thus, according to the optical image measurement device 80, it is possible to image the microstructure of a deep tissue of the measured object.

Further, by using a flexible fiber as the optical fiber bundle 113, it is possible to favorably insert the optical fiber bundle 113 into a subject body, for example.

[Modification]

A modification of the optical image measurement device according to this embodiment will be described.

Although the optical image measurement device 80 used for acquiring an image of the fundus oculi has been described in detail in the aforementioned second embodiment, the optical image measurement device according to this embodiment is not limited to that.

Figure 8:
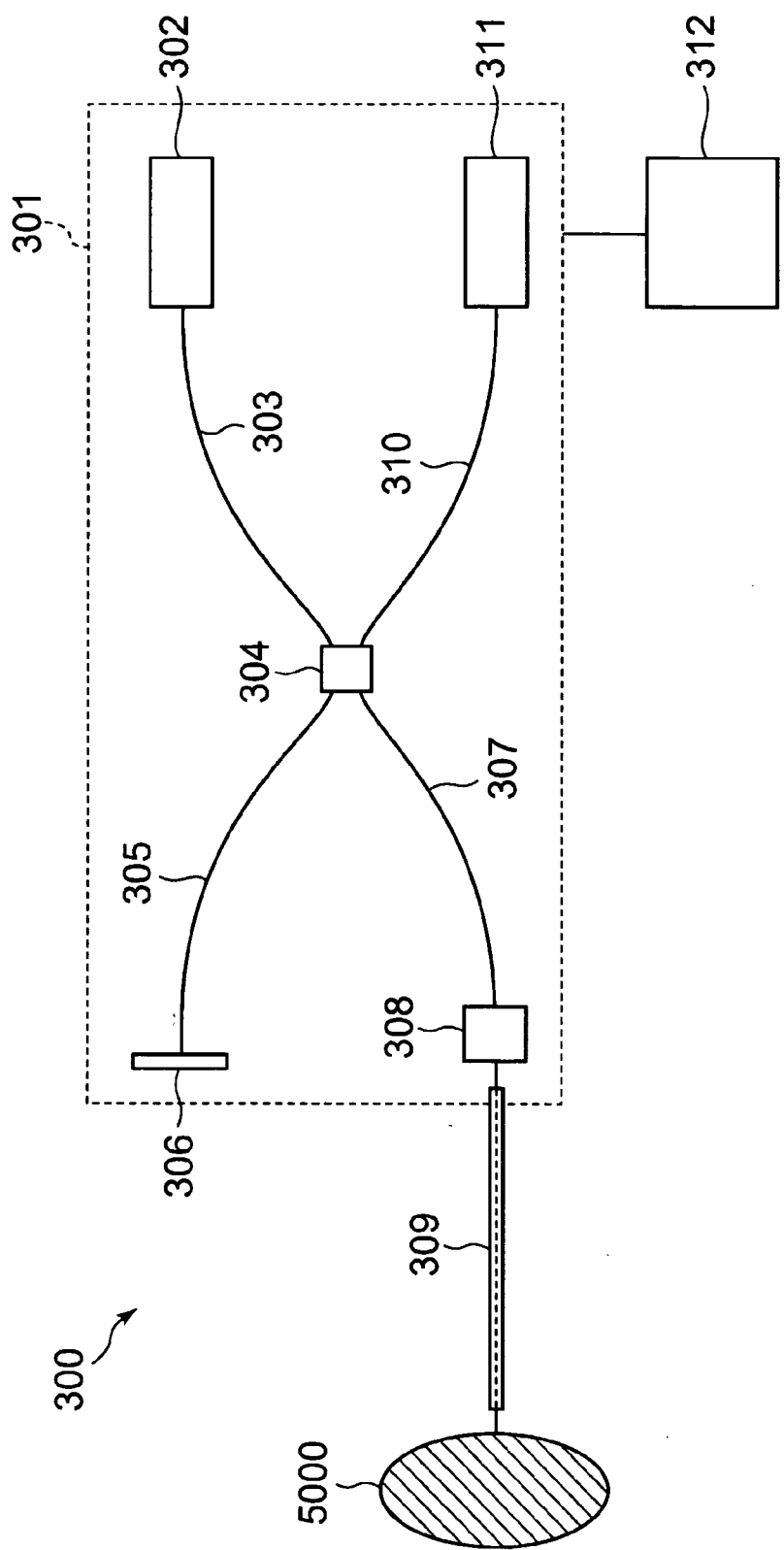
FIG. 8 is a schematic view illustrating an example of the configuration of a modification of the second embodiment of the optical image measurement device according to the present invention.

An example of the optical image measurement device according to this embodiment is shown in FIG. 8. An optical image measurement device 300 has an optical system unit 301 and a computer 312. The computer 312 executes control of the optical system unit 301.

A low-coherence light outputted from a low-coherence light source 302 is guided to an optical coupler 304 by an optical fiber 303. The optical coupler 304 splits this low-coherence light into the signal light and the reference light.

The reference light is guided to a reference mirror 306 by an optical fiber 305 and is reflected. This reflected light is guided to the optical coupler 304 by the optical fiber 305.

The signal light is guided to a scan unit 308 by an optical fiber 307. As in the first embodiment, an optical fiber bundle 309 is composed of a bundle of optical fibers (refer to FIG. 2). The scan unit 308 makes the signal light enter the base end part (the end part on the scan unit 308 side) of one (or two or more) of the plurality of optical fibers.

The scan unit 308 may have a configuration including a Galvano mirror and so on as in the scan unit 141 of the above-mentioned embodiment, or may have another configuration. That is to say, as far as acting to guide the signal light sequentially to the plurality of fibers included in the optical fiber bundle 309, the scan unit 308 may have any configuration.

The signal light guided by a certain optical fiber of the optical fiber bundle 309 is converted into a focused light by a microlens at the top end part of the optical fiber, and reflected or scattered around a depth position to be observed of the measured object 5000. The reflected light and the scattered light enter the top end part of the optical fiber to be guided by the optical fiber, and return to the optical coupler 304 via the scan unit 308 and the optical fiber 307.

The optical coupler 304 superimposes the reference light and the signal light with each other to generate an interference light. This interference light is guided to a spectrometer 311 by an optical fiber 310. The spectrometer 311 detects the spectral components of this interference light, and outputs the detection signals to the computer 312.

The computer 312 forms a one-dimensional image along the depth direction at the site where the signal light is reflected and dispersed, based on this detection signal.

The optical image measurement device 300 repeatedly executes measurements by causing the scan unit 308 to sequentially make the signal light enter the plurality of optical fibers included in the optical fiber bundle 309. The spectrometer 311 sequentially detects the spectral components of the interference light corresponding to the plurality of optical fibers. The computer 312 sequentially forms one-dimensional images along the depth direction at different positions of the measured object 5000, based on the detection signals sequentially outputted from the spectrometer 311. Furthermore, the computer 312 forms a tomographic image of the measured object 5000 based on these one-dimensional images.

According to the optical image measurement device 300, similarly to the optical image measurement device 80 according to the second embodiment, it is possible to image the microstructure of a deep tissue of the measured object.

An optical member for matching the optical path length of the signal light with that of the reference light may be disposed on the optical path of the reference light, for example. Further, an optical member for matching the influence of dispersion applied to the signal light with the influence of dispersion applied to the reference light may be disposed on the optical path of the reference light, for example.

Figure 9:
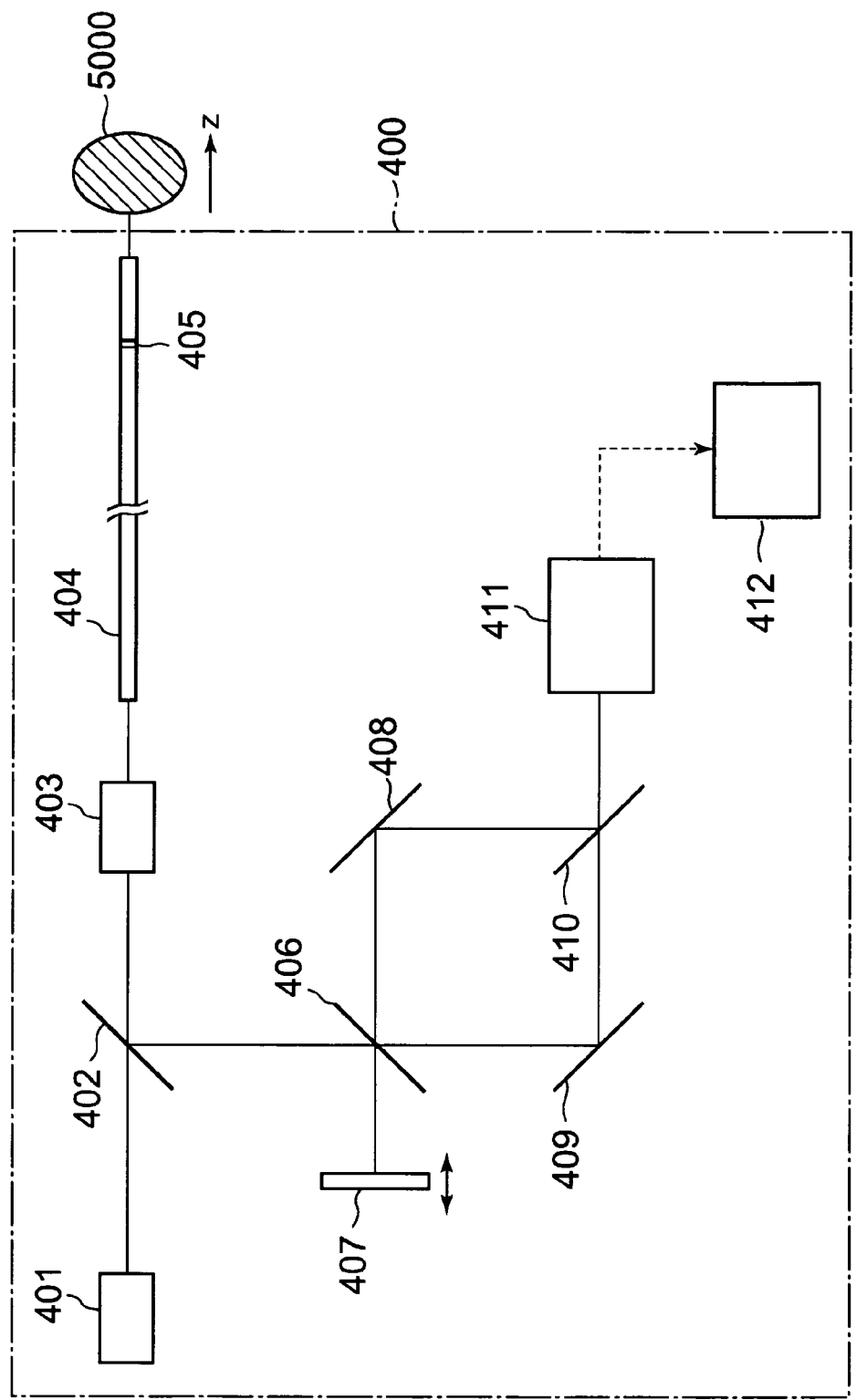
FIG. 9 is a schematic view illustrating an example of the configuration of a modification of the second embodiment of the optical image measurement device according to the present invention.
Figure 10:
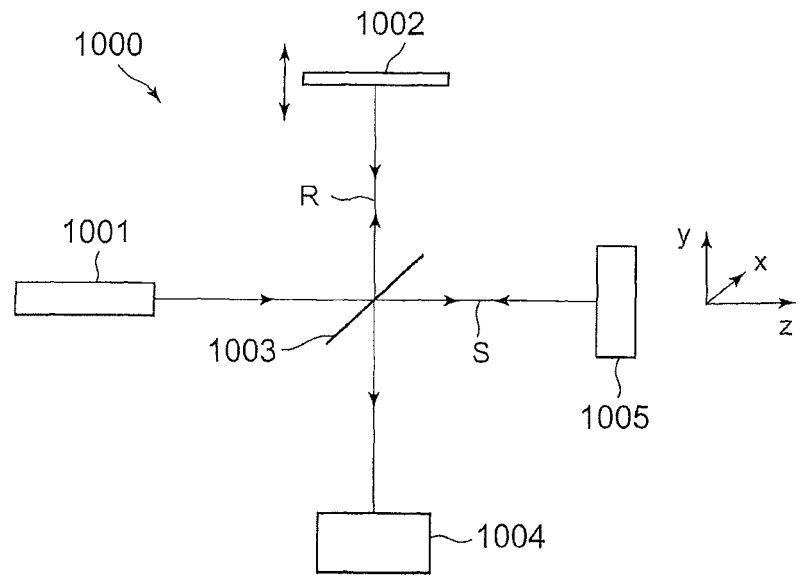
FIG. 10 is a schematic view illustrating an example of the configuration of a conventional optical image measurement device.
Figure 11:
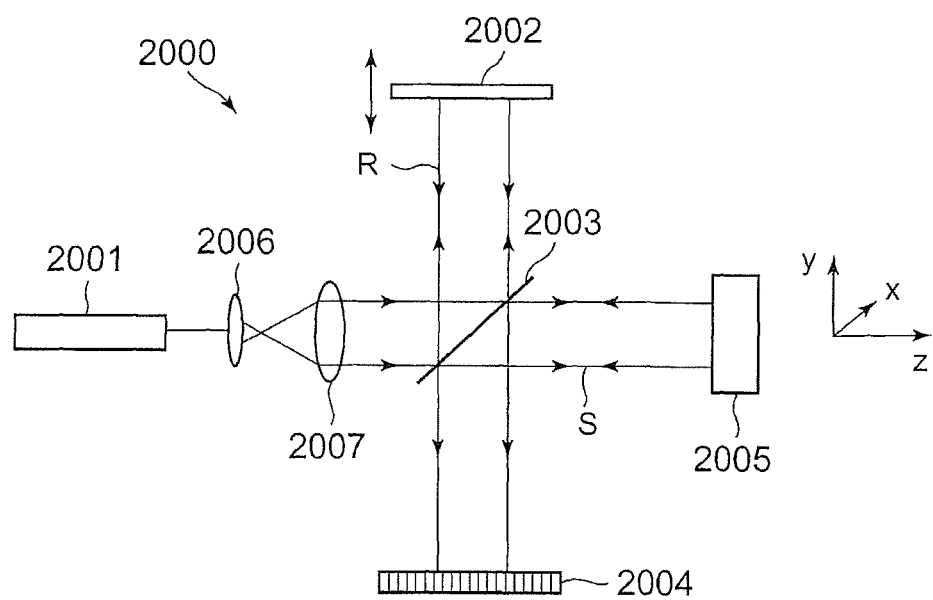
FIG. 11 is a schematic view illustrating an example of the configuration of a conventional optical image measurement device.

Another example of the optical image measurement device according to this embodiment is shown in FIG. 9. This modification relates to a configuration in which the optical fiber bundle is provided with a splitter.

A low-coherence light outputted from a low-coherence light source 401 of an optical image measurement device 400 shown in FIG. 9 is transmitted through a beam splitter 402 to enter a scan unit 403.

As in the above embodiment, the scan unit 403 scans the base end part (the end part on the scan unit 403 side) of an optical fiber bundle 404 with the low-coherence light. That is to say, the scan unit 403 sequentially makes the low-coherence light enter a plurality of optical fibers included in the optical fiber bundle 404.

The optical fiber bundle 404 is provided with a reflector 405. The reflector 405 reflects part of the low-coherence light traveling toward the top end part in the optical fiber bundle 404. The low-coherence light reflected by the reflector 405 is used as the reference light. On the other hand, the low-coherence light transmitted through the reflector 405 is used as the signal light. The reflector 405 is an example of the "splitter" and the "reflector" of the present invention.

As in the first embodiment, the reflector 405 can be installed at any position of the optical fiber bundle 404.

The reference light composed of the low-coherence light reflected by the reflector 405 exits from the base end part of the optical fiber bundle 404, travels through the scan unit 403, and is reflected by the beam splitter 402. Furthermore, the reference light is reflected by a beam splitter 406 to reach a reference mirror 407.

The reference light reflected by the reference mirror 407 is transmitted through the beam splitter 406 to reach a beam splitter 410.

The reference mirror 407 is configured to be movable in the direction of an arrow pointing to both sides in FIG. 9. Consequently, it is possible to acquire images at various depth positions of the measured object 5000.

On the other hand, the signal light composed of the low-coherence light transmitted through the reflector 405 exits from the top end part of the optical fiber bundle 404. A microlens is disposed to the top end part of each optical fiber included in the optical fiber bundle 404.

The signal light radiated to the measured object 5000 is reflected and scattered at various depth positions of the measured object 5000. The reflected light and the scattered light of this signal light enter the optical fiber through the microlens. Furthermore, the signal light is guided by the optical fiber to exit from the base end part.

The signal light emitted from the base end part travels through the scan unit 403, is reflected by the beam splitter 402, is transmitted through the beam splitter 406, is reflected by a reflection mirror 409, and reaches the beam splitter 410.

The reference light reflected by the beam splitter 410 and the signal light transmitted through the beam splitter 410 are superimposed with each other to generate an interference light. This interference light is guided to a spectrometer 411 and the spectral components thereof are detected.

The spectrometer 411 sends the result of detection of the spectral components (the detection signals) of the interference light to a computer 412. The spectrometer 411 is an example of the "detector" of the present invention.

The computer 412 forms a one-dimensional image along the depth direction at the site where the signal light has been reflected and dispersed, based on the detected signals from the spectrometer 411.

The optical image measurement device 400 repeatedly executes measurements by causing the scan unit 403 to sequentially make the low-coherence light enter a plurality of optic fibers included in the optical fiber bundle 404. The spectrometer 411 sequentially detects the spectral components of the interference light corresponding to the plurality of optical fibers. The computer 412 sequentially forms one-dimensional images along the depth direction at different positions of the measured object 5000, based on the detected signals sequentially outputted from the spectrometer 411. Furthermore, the computer 412 forms a tomographic image of the measured object 5000 based on these one-dimensional images.

According to the optical image measurement device 400, as in the optical image measurement device 80 according to the second embodiment, it is possible to image the microstructure of a deep tissue of the measured object.

It is also possible to dispose an optical member for matching the optical path length of the signal light with the optical path length of the reference light on the optical path of the reference light, for example. Further, it is also possible to dispose an optical member for matching the influence of dispersion applied to the signal light with the influence applied to the reference light on the optical path of the reference light, for example.

A swept-source type optical image measurement device is configured in a substantially similar manner to the Fourier-domain type optical image measurement device described above. That is to say, the swept-source type optical image measurement device is provided with a light source (a high-speed wavelength scanning laser) that switches lights of various frequencies at high speeds to output, and is configured to detect the interference light based on each frequency of light to form a tomographic image of the measured object based on the detection result.

Although it is desirable to make the signal light (or the low-coherence light) accurately enter each of the plurality of optical fibers included in the optical fiber bundle in the optical image measurement device according to this embodiment, a highly accurate control is required therefor. In particular, when the interval between adjacent optical fibers is small, it is necessary to execute control with extremely high accuracy. Therefore, it is possible to configured to scan the end surface of the base end part of the optical fiber bundle (the surface of arrangement of the base end parts of the plurality of optical fibers) with the signal light (or the low-coherence light) with predetermined accuracy, and to form an image based on only a favorable interference light obtained thereby. The favorable interference light refers to, for example, an interference light having an intensity of a predetermined value or more.

The invention claimed is:

1. An optical image measurement device, comprising:
    an interference light generator configured to split a light from a broadband light source into a signal light and a reference light, and superimpose the signal light reflected by a measured object and the reference light reflected by a reference object to generate an interference light;
    a detector configured to detect the interference light;
    an image forming part configured to form an image of the measured object based on a detection result of the interference light,
    wherein the interference light generator includes a light guiding part including a flexible optical fiber bundle configured to emit the signal light split from the light from the broadband light source from a first end and guide the signal light reflected by the measured object and entered into the first end, and the interference light generator is configured to superimpose the guided signal light and the reference light to generate an interference light,
    a micro-lens is provided on the first end of each fiber of the optical fiber bundle;
    the light guiding part includes a splitter configured to split a light having entered from the second end into a signal light and a reference light, and the light guiding part is configured to guide the signal light reflected by the measured object and entered into the first end to the second end and emit the signal light therefrom and is configured to emit the reference light from the second end, and
    the interference light generator is configured to superimpose the signal light and the reference light emitted from the second end, respectively, to generate the interference light;
    the interference light generator comprising:
    an illumination optical system that emits illumination light onto the measurement object, sharing a part of the light path of the signal light; and
    an imaging optical system that guides illumination light reflected from the measurement object, sharing a part of the light path of the signal light.

2. The optical image measurement device according to claim 1, wherein:
    the splitter includes a reflecting part configured to reflect part of the light from the light source guided to the first end and split the light into a signal light and a reference light.

3. The optical image measurement device according to claim 1, wherein the detector includes a two-dimensional photosensor array configured to simultaneously detect a plurality of interference lights based on a plurality of signal lights guided by a plurality of fibers included in the flexible optical fiber bundle.

4. The optical image measurement device according to claim 1, wherein the interference light generator includes an optical member for matching an optical path length of the signal light with an optical path length of the reference light.

5. The optical image measurement device according to claim 4, wherein the optical member is disposed on an optical path of the reference light.

6. The optical image measurement device according to claim 1, wherein the interference light generator includes an optical member for matching an influence of dispersion applied to the signal light with an influence of dispersion applied to the reference light.

7. The optical image measurement device according to claim 6, wherein the optical member is disposed on an optical path of the reference light.

* * * * *